US010898476B2

(12) United States Patent
Jensen et al.

(10) Patent No.: US 10,898,476 B2
(45) Date of Patent: Jan. 26, 2021

(54) HEAT SHOCK PROTEINS AND CHOLESTEROL HOMEOSTASIS

(71) Applicant: Orphazyme A/S, Copenhagen N (DK)

(72) Inventors: Thomas Kirkegaard Jensen, Rødovre (DK); Elina Ikonen, Helsinki (FI); Burcin Gungor, Helsinki (FI)

(73) Assignee: Orphazyme A/S, Copenhagen N (DK)

( * ) Notice: Subject to any disclaimer, the term of this patent is extended or adjusted under 35 U.S.C. 154(b) by 0 days.

(21) Appl. No.: 16/093,283

(22) PCT Filed: Apr. 10, 2017

(86) PCT No.: PCT/DK2017/050114
§ 371 (c)(1),
(2) Date: Oct. 12, 2018

(87) PCT Pub. No.: WO2017/178029
PCT Pub. Date: Oct. 19, 2017

(65) Prior Publication Data
US 2019/0201389 A1 Jul. 4, 2019

(30) Foreign Application Priority Data
Apr. 13, 2016 (DK) .................... 2016 70223

(51) Int. Cl.
| A61K 38/00 | (2006.01) |
| A61K 31/4545 | (2006.01) |
| A61K 38/17 | (2006.01) |
| A61K 31/5395 | (2006.01) |
| A61K 31/00 | (2006.01) |
| A61P 3/06 | (2006.01) |

(52) U.S. Cl.
CPC .......... *A61K 31/4545* (2013.01); *A61K 31/00* (2013.01); *A61K 31/5395* (2013.01); *A61K 38/1709* (2013.01); *A61P 3/06* (2018.01)

(58) Field of Classification Search
None
See application file for complete search history.

(56) References Cited

U.S. PATENT DOCUMENTS

| 5,348,945 A | 9/1994 | Berberian et al. |
| 5,830,464 A | 11/1998 | Srivastava |
| 5,948,646 A | 9/1999 | Srivastava |
| 5,985,270 A | 11/1999 | Srivastava |
| 6,007,821 A | 12/1999 | Srivastava et al. |
| 6,139,841 A | 10/2000 | Srivastava |
| 6,187,312 B1 | 2/2001 | Srivastava |
| 6,375,953 B1 | 4/2002 | Srivastava et al. |
| 6,384,029 B1 | 5/2002 | Jednakovits et al. |
| 6,403,095 B1 | 6/2002 | Srivastava et al. |
| 6,475,490 B1 | 11/2002 | Srivastava et al. |
| 6,649,628 B1 | 11/2003 | Kurthy et al. |
| 6,653,326 B1 | 11/2003 | Vigh et al. |
| 6,855,802 B1 | 2/2005 | Triebel et al. |
| 7,070,785 B2 | 7/2006 | Lehner et al. |
| 7,125,843 B2 | 10/2006 | DeFrees et al. |
| 7,126,002 B2 | 10/2006 | Urogdi et al. |
| 7,148,239 B2 | 12/2006 | Vigh et al. |
| 7,326,574 B2 | 2/2008 | Boux et al. |
| 7,361,655 B2 | 4/2008 | Csakai et al. |
| 7,384,936 B2 | 6/2008 | Csakai et al. |
| 7,396,681 B1 | 7/2008 | Multhoff |
| 7,517,948 B2 | 4/2009 | Multhoff |
| 7,550,457 B2 | 6/2009 | Csakai et al. |
| 7,691,849 B2 | 4/2010 | Csakai et al. |
| 7,745,465 B2 | 6/2010 | Vigh et al. |
| 7,750,050 B2 | 7/2010 | Schuchman et al. |
| 9,662,375 B2 | 5/2017 | Jensen et al. |
| 2001/0034042 A1 | 10/2001 | Srivastava |
| 2002/0006410 A1 | 1/2002 | Lukacs et al. |
| 2002/0035072 A1 | 3/2002 | Fan et al. |
| 2002/0037290 A1 | 3/2002 | Armen |
| 2002/0039583 A1 | 4/2002 | Subjeck et al. |
| 2002/0095135 A1 | 7/2002 | Meeker et al. |
| 2002/0119163 A1 | 8/2002 | Srikumaran |
| 2002/0127219 A1 | 9/2002 | Okkels et al. |
| 2002/0127718 A1 | 9/2002 | Kuppner et al. |
| 2002/0156250 A1 | 10/2002 | Wallen et al. |
| 2002/0172682 A1 | 11/2002 | Srivastava |
| 2002/0192230 A1 | 12/2002 | Srivastava |
| 2003/0012794 A1 | 1/2003 | Srivastava et al. |
| 2003/0035808 A1 | 2/2003 | Srivastava |
| 2003/0073094 A1 | 4/2003 | Young et al. |

(Continued)

FOREIGN PATENT DOCUMENTS

| EP | 0751957 | 9/1995 |
| EP | 2145896 | 1/2010 |

(Continued)

OTHER PUBLICATIONS

Balogh et al.; The hyperfluidization of mammalian cell membranes acts as a signal to initiate the heat shock protein response. FEBS Journal 272 (2005) 6077-6086.
Botzler et al.; Synergistic effects of heat and ET-18-OCH3 on membrane expression of hsp70 and lysis of leukemic K562 cells. Experimental Hematology 27 (1999) 470-478.
Brunk et al.: Lysosomal involvement in apoptosis. Redox Rep. 2001; 6(2):91-7.
Brunk et al.: Photo-oxidative disruption of lysosomal membranes causes apoptosis of cultured human fibroblasts. Free Radical Biology & Medicine. vol. 23, No. 4, pp. 616-626, 1997.
Chung et al.; HSP72 protects against obesity-induced insulin resistance. PNAS Feb. 5, 2008 vol. 105, No. 5, 1739-1744.
Daugaard et al., "The heat shock protein 70 family: Highly homologous proteins with overlapping and distinct functions," Febs Letters, Elsevier, Amsterdam, vol. 581, No. 19, Jul. 31, 2007, pp. 3702-3710.

(Continued)

*Primary Examiner* — Jeanette M Lieb
(74) *Attorney, Agent, or Firm* — Cooley LLP; Heidi A. Erlacher; Christine E. Dunne

(57) ABSTRACT

Provided herewith are bioactive agents that increase the intracellular concentration and/or activity of one or more heat shock proteins, including Hsp70, for use in the treatment of a disease associated with dysregulation of cholesterol homeostasis.

12 Claims, 9 Drawing Sheets

Specification includes a Sequence Listing.

(56) References Cited

U.S. PATENT DOCUMENTS

| | | |
|---|---|---|
| 2003/0129196 A1 | 7/2003 | Srivastava |
| 2003/0203846 A1 | 10/2003 | Srivastava et al. |
| 2003/0216315 A1 | 11/2003 | Nicchitta et al. |
| 2003/0236300 A1 | 12/2003 | Caplan et al. |
| 2004/0022796 A1 | 2/2004 | Srivastava |
| 2004/0047876 A1 | 3/2004 | Srivastava |
| 2005/0048608 A1 | 3/2005 | Chan et al. |
| 2005/0112640 A1 | 5/2005 | Davidson et al. |
| 2005/0153906 A1 | 7/2005 | Bedwell et al. |
| 2005/0202044 A1 | 9/2005 | Mizzen et al. |
| 2005/0267020 A1 | 12/2005 | Faure et al. |
| 2006/0009520 A1 | 1/2006 | Tall et al. |
| 2006/0089302 A1 | 4/2006 | Abulafia-Lapid et al. |
| 2006/0093612 A1 | 5/2006 | Srivastava |
| 2006/0264609 A1 | 11/2006 | Lehner et al. |
| 2006/0270833 A1 | 11/2006 | Henot et al. |
| 2007/0231337 A1 | 10/2007 | Multhoff |
| 2008/0009516 A1 | 1/2008 | Wustman |
| 2008/0014191 A1 | 1/2008 | Balch et al. |
| 2008/0019915 A1 | 1/2008 | Hadida-Ruah et al. |
| 2008/0026012 A1 | 1/2008 | Podack et al. |
| 2008/0039400 A1 | 2/2008 | Van Eden et al. |
| 2008/0039497 A1 | 2/2008 | Greensmith et al. |
| 2008/0132450 A1 | 6/2008 | Lee et al. |
| 2008/0161258 A1 | 7/2008 | Henning et al. |
| 2008/0305084 A1 | 12/2008 | Podsakoff et al. |
| 2009/0163500 A1 | 6/2009 | Lingwood et al. |
| 2009/0203065 A1 | 8/2009 | Gehman et al. |
| 2009/0203605 A1 | 8/2009 | Segatori et al. |
| 2009/0208524 A1 | 8/2009 | Srivastava et al. |
| 2009/0227572 A1 | 9/2009 | Barber et al. |
| 2009/0298857 A1 | 12/2009 | Chiosis et al. |
| 2009/0318343 A1 | 12/2009 | Garigapati et al. |
| 2010/0004277 A1 | 1/2010 | Bulawa et al. |
| 2010/0087490 A1 | 4/2010 | Young |
| 2010/0130730 A1 | 5/2010 | Garigapati et al. |
| 2010/0168016 A1 | 7/2010 | Ackerman et al. |
| 2010/0196279 A1 | 8/2010 | Lockhart |
| 2010/0221225 A1 | 9/2010 | Byrne et al. |
| 2010/0266571 A1 | 10/2010 | Lockhart et al. |
| 2010/0317690 A1 | 12/2010 | Kawamura et al. |
| 2010/0329985 A1 | 12/2010 | Van Eden et al. |
| 2011/0027254 A1 | 2/2011 | Daniel et al. |
| 2011/0028403 A1 | 2/2011 | Le Poole et al. |
| 2011/0081428 A1 | 4/2011 | Lithgow et al. |
| 2011/0105560 A1 | 5/2011 | Wustman |
| 2011/0110938 A1 | 5/2011 | Chiu et al. |
| 2011/0123512 A1 | 5/2011 | Prahlad et al. |
| 2011/0286993 A1 | 11/2011 | Jensen et al. |
| 2012/0115908 A1 | 5/2012 | Greensmith et al. |
| 2013/0230506 A1* | 9/2013 | Jensen ............... A61K 31/4545 424/94.3 |
| 2014/0080769 A1* | 3/2014 | Platt ..................... C07D 211/94 514/24 |
| 2015/0126551 A1 | 5/2015 | Greensmith et al. |
| 2015/0284472 A1 | 10/2015 | Sardi et al. |

FOREIGN PATENT DOCUMENTS

| | | |
|---|---|---|
| EP | 2318032 | 4/2012 |
| EP | 24843 | 8/2012 |
| EP | 2659904 A1 | 11/2013 |
| EP | 2481400 B1 | 6/2014 |
| WO | WO-1997016439 | 5/1997 |
| WO | WO-2000/35914 A1 | 6/2000 |
| WO | WO-2000050403 | 8/2000 |
| WO | WO-200117554 | 3/2001 |
| WO | WO-200134184 | 5/2001 |
| WO | WO-200152877 | 7/2001 |
| WO | WO-200152890 | 7/2001 |
| WO | WO-200234777 | 5/2002 |
| WO | WO-2003026653 A1 | 4/2003 |
| WO | WO-2003049692 | 6/2003 |
| WO | WO-2003/061684 | 7/2003 |
| WO | WO-2003086452 | 10/2003 |
| WO | WO-2005/041965 A1 | 5/2005 |
| WO | WO-2005120568 | 12/2005 |
| WO | WO-2007041285 | 4/2007 |
| WO | WO-2007/150064 | 12/2007 |
| WO | WO-2008021210 | 2/2008 |
| WO | WO-2008112525 | 9/2008 |
| WO | WO-2008117026 | 10/2008 |
| WO | WO-2009095452 | 8/2009 |
| WO | WO-2009100037 | 8/2009 |
| WO | WO-2009137721 | 11/2009 |
| WO | WO-2009137796 | 11/2009 |
| WO | WO-2009141627 | 11/2009 |
| WO | WO-2009155936 | 12/2009 |
| WO | WO-2010015816 | 2/2010 |
| WO | WO-2010022461 | 3/2010 |
| WO | WO-2010053655 | 5/2010 |
| WO | WO-2010086418 | 8/2010 |
| WO | WO-2010092112 | 8/2010 |
| WO | WO-2010102988 | 9/2010 |
| WO | WO 2010116141 | 10/2010 |
| WO | WO-2010148253 | 12/2010 |
| WO | WO-2011019763 | 2/2011 |
| WO | WO-2011075686 | 6/2011 |
| WO | WO-2012/012656 A2 | 1/2012 |
| WO | WO-2012/072082 A1 | 6/2012 |
| WO | WO-2013/006076 A1 | 1/2013 |
| WO | WO-2013/148333 A1 | 10/2013 |
| WO | WO-2014/071282 A1 | 5/2014 |
| WO | WO-2016/041561 A1 | 3/2016 |

OTHER PUBLICATIONS

Ferlinz et al.; Stimulation of lysosomal sphingomyelin degradation by sphingolipid activator proteins. Chemistry and Physics of Lipids 102 (1999) 35-43.

Fleshner & Johnson: Endogenous extra-cellular heat shock protein 72: Releasing signal(s) and function. Int. J. Hyperthermia, Aug. 2005; 21(5):457-471.

Gehrmann et al.; Differential Up-Regulation of Cytosolic and Membrane-Bound Heat Shock Protein 70 in Tumor Cells by Anti-Inflammatory Drugs. Clinical Cancer Research vol. 10, 3354-3364, May 15, 2004.

Gehrmann et al.; Effects of Antineoplastic Agents on Cytoplasmic and Membrane-Bound Heat Shock Protein 70 (Hsp70) Levels. Biol. Chem., vol. 383, pp. 1715-1725, Nov. 2002.

Gehrmann et al.; The therapeutic implications of clinically applied modifiers of heat shock protein 70 (Hsp70) expression by tumor cells. Cell Stress and Chaperones (2008) 13L 1-10.

Harada et al,: Heat shock proteins and the antitumor T cell response. Biotherapy 10: 229-235, 1998.

Kalmar & Greensmith; Activation of the heath shock response in a primary cellular model of motoneuron neurodegeneration—evidence for neuroprotective and neurotoxic effects. Cellular Molecular Biology Letters vol. 14 (2009) pp. 319-335.

Kalmar et al.; Late stage treatment with arimoclomol delays disease progression and prevents protein aggregation in the SOC1G93A mouse model of ALS. Journal of Neurochemistry 2008, 107, 339-350.

Kalmar et al.; Upregulation of Heat Shock Proteins Rescues Motoneurons from Axotomy-Induced Cell Death in Neonatal Rats. Experimental Neurology 176, 87-97 (2002).

Kieran et al., Treatment with arimoclomol, a coinducer of heat shock proteins, delays disease progression in ALS mice, Nature Medicine, 10(4): 402-45, Apr. 2004.

Kirkegaard et al., Hsp70 stabilizes lysosomes and reverts Niemann-Pick disease-associated lysosomal pathology, Nature Letters, 463: 549-554, Jan. 28, 2010.

Kirkegaard-Sorenson; Hsp70 binding to BMP—A novel mechanism for cellular protection. Dep. of Apoptosis, Danish Cancer Society, Feb. 2008. PhD Thesis. University of Copenhagen, Faculty of Health Sciences.

Kobayashi et al.: A lipid associated with the antiphospholipid syndrome regulates endosome structure and function. Nature Letters, vol. 392 Mar. 12, 1998.

(56) References Cited

OTHER PUBLICATIONS

Kolzer et al.: Interactions of acid sphingomyelinase and lipid bilayers in the presence of the tricyclic anyidepressant desipramine, FEBS Letters 559 (2004) 96-98.

Nylandsted et al.: Heat shock protein 70 promotes cell survival by inhibiting lysosomal membrane permeabilization. J. Exp. Med. vol. 200, No. 4, Aug. 16, 2004 425-435.

Ohtsuka et al.; Inducers and co-inducers of molecular chaperones, Int. J. Hyperthermia, Dec. 2005; 21(8): 703-711.

Sambrook et al., Molecular Cloning, A Laboratory Manual, Cold Spring Harbor, Laboratory Press (1998), 1.101-1.104

Tavaria et al.: A hitchhiker's guide to the human Hsp70 family. Mini- review, Cell stress & Chaperones (1996) 1 (1), 23-28.

Tidwell et al.: Administration of Hsp70 in vivo inhibits motor and sensory neuron degeneration. Cell Stress & Chaperones(2004) 9(1), 88-98.

Tytell & Hooper; Heat Shock proteins: new keys to the development of cytoprotective therapies. Expert Opin Ther Targets, Apr. 2001;5(2):267-87.

Tytell: Release of heat shock proteins (Hsps) and the effects of extracellular Hsps on neural cells and tissues. Int J Hypothermia, Aug. 2005; 21(5): 445-455.

Torok et al.; Heat shock protein coinducers with no effect on protein denaturation specifically modulate the membrane lipid phase. PNAS Mar. 18, 2003, vol. 100, No. 6, 3131-3136.

Vigh et al., Bimoclomol: A nontoxic, hydroxylamine derivative with stress protein-inducing activity and cytoprotective effects, Nature Medicine, 3(10): 1150-54, Oct. 1997.

Vigh at al.; Can the stress protein response be controlled by membrane-lipid therapy?; Trends in Biochemical Sciences vol. 32 No. 8 (2007).

Wei et al., Inhibition of proliferation and induction of apoptosis by abrogation of heat-shock protein (HSP) 70 expression in tumor cells. Cancer Immunol. Immunother. (1995) 40:73-78.

Yu et al.: Retinal uptake of intravitreally injected Hsc/Hsp70 and its effects on susceptibility to light damage. Molecular Vision 2001; 7:48-56.

Communication Pursuant to Article 94(3) EPC for Application No. 09768858.4 dated Jul. 26, 2011.

Du, W. et al., Cell Growth Inhibition by Farnseyltransferase Inhibitors is Mediated by Gain of Geranylgeranylated RhoB, *Molecular and Cellular Biology*, 19(3): 1831-40, Mar. 1999.

Prendergast, G. et al., Farnesyltransferase Inhibition Causes Morphological Reversion of ras-Transformed Cells by a Complex Mechanism that Involves Regulation of the Actin Cytoskeleton, *Molecular and Cellular Biology*, 14(6): 4193-4202, Jun. 1994.

Balabanov, S. et al., Quantitative proteomics analysis of BMS-214662 effects on CD34 positive cells from chronic myeloid leukaemia patients, *Proteomics*, 13: 153-68, 2013.

Mazieres, J. et al., Perspectives on farnesyl transferase inhibitors in cancer therapy, *Cancer Letters*, 206: 159-67, 2004.

Porcu, G. et al., A yeast-based genomic strategy highlights the cell protein networks altered by FTase inhibitor peptidomimetics, *Molecular Cancer*, 9: 197, 2010.

Horvath, I. et al., Membrane-associated stress proteins: More than simply chaperones, *Biochimica et Biophysica Acta*, 1778: 1653-64, 2008.

Simons, K. et al., Jamming the Endosomal System: Lipid Rafts and Lysosomal Storage Diseases, *Trends in Cell Biology*, 10: 459-62 2000.

Goni, F. et al., Sphingomyelinases: enzymology and membrane activity, Federation of European Biochemical Societies, 531: 38-46, 2002.

Yenari, M. et al., The neuroprotective potential of heat shock protein 70 (HSP70), Molecular Medicine Today, 5: 525-31, 1999.

Keeling et al., Gentamicin-mediated suppression of Hurler syndrome stop mutations restores a low level of alpha-L-iduronidase activity and reduces lysosomal glycosaminoglycan accumulation, Human Molecular Genetics, 10: 291-99, 2001.

Meikle et al., Effect of lysosomal storage on bis(monoacylglycero)phosphate, Biochem J., 411: 71-78, 2008.

Voellmy et al., Isolation and functional analysis of a human 70,000-dalton heat shock protein segment, Proc. Natl. Acad. Sci. USA, 82: 4949-53, 1985.

Wu, et al., Structure and expression of the human gene ancoding major heat shock protein HSP70, Mol. Cell. Biol., 5(2): 330-41, 1985.

Winchester, B. et al., The molecular basis of lysosomal storage disease, *Biochemical Society Transactions*, 28: 150-54, 2000.

Au, Q. et al., High-content image-based screening for small-molecule chaperone amplifiers in heat shock, *Journal of Biomolecular Screening*, 13(19) 953-959, 2008.

Bruening, W. et al., Up-regulation of protein chaperones preserves viability of cells expressing toxic Cu/Zn-superoxide dismutase mutants associated with amyotrophic lateral sclerosis, *Journal of Neurochemistry*, 72: 693-99, 1999.

Horváth, I. et al., Cell biology: Stability in times of stress, *Nature*, 463(7280): 436-438, 2010.

Polakowski, J. et al., Bimoclomol elevates heat shock protein 70 and cytoprotects rat neonatal cardiomyocytes, European Journal of Pharmacology, 435: 73-77, 2002.

Hallows, J. et al., p35/p25 Is Not Essential for Tau and Cytoskeletal Pathology or Neuronal Loss in Niemann-Pick Type C Disease, The Journal of Neuroscience, 26: 2738-2744. 2006.

Parfitt, D. et al., The heat-shock response co-inducer arimoclomol protects against retinal degeneration in rhodopsin retinitis pigmentosa, Cell Death and Disease, 5: 1-10, 2014.

Patterson, M. et al., Miglustat for treatment of Niemann-Pick C disease: a randomised controlled study, Lancet, Neurology, 6: 765-772, 2007.

Kabakov, A. et al., Pharmacological attenuation of apoptosis in reoxygenated endothelial cells, Cellular and Molecular Life Sciences, 61: 3076-86, 2004.

Cohen, F. et al., Therapeutic approaches to protein-misfolding diseases, Nature, 426: 905-909, 2003.

Freeman, B. et al., The human cytosolic molecular chaperones hsp90 (hsc70) and hdj-1 have distinct roles in recognition of a non-native protein and protein refolding, The European Molecular Biology Journal, 15: 2969-79, 1996.

Kirkegaard-Sorenson et al.; Interaction between Hsp70 and bis(monoacylglycero)phosphate stabilizes lysosomes and promotes cell survival. APMIS, 116(5): 436-437, 2008.

Ng et al., Predicting deleterious amino acid substitutions. Genome Res. 2001 11: 863-874.

Zhu Yunxiang et al. "Dexmethasone-mediated up-regulation of the mannose receptor improves the delivery of recombinant glucocerebrosidase to Gaucher macrophages," The Journal of Pharmacology and Experimental Therapeutics, Feb. 2004, vol. 308, No. 2, pp. 705-711.

Jaatela, M. et al., Emerging Role of Heat Shock Proteins in Biology and Medicine, *Annals of Medicine*, 24: 249-258, 1992.

Hu, W. et al., Proteomic identification of heat shock protein 70 as a candidate target for enhancing apoptosis induced by farnesyl transferase inhibitor. *Proteomics*, 3: 1904-11, 2003.

Kalmar, B. et al., The effect of treatment with BRX-220, a co-inducer of heat shock proteins, on sensory fibers of the rat following peripheral nerve injury, *Exp. Neurol.*, 184 636-647, 2003.

Rakonczay, Z. et al., Nontoxic heat shock protein coinducer BRX-220 protects against acute pancreatitis in rats, *Free Radical Biology and Medicine*, 32(12): 1283-1292, 2002.

Lubbers, N. et al., Oral bimoclomol elevates heat shock protein 70 and reduces myocardial infarct size in rats, *European Journal of Pharmacology*, 435: 79-83, 2002.

Cudkowicz, M. et al., Arimoclomol at Dosages up to 300 Mg/day is Well Tolerated and Safe in Amyotrophic Lateral Sclerosis, *Muscle & Nerve*, pp. 837-844, Jul. 2008.

Lepist, E. et al., Contribution of the organic anion transporter OAT2 to the renal active tubular secretion of creatinine and mechanism for serum creatinine elevations caused by cobicistat, *Kidney International*, 86: 350-357, 2014.

(56) References Cited

OTHER PUBLICATIONS

Roth, A. et al., Interaction between Hsp70 and bis(monoacylglycero)phosphate stabilizes lysosomes and promotes cell survival, APMIS, 116: 437, 2008.
Balwani, M. et al., Gaucher disease: When molecular testing and clinical presentation disagree—the novel c.1226A.>G(p. N370S)-RecNcil allele, J Inherit Metab Dis, 34:789-793, 2011.
Bergamin, N. et al., A human neuronal model of Niemann Pick C disease developed from stem cells isolated from patient's skin, Orphanet Journal of Rare Diseases, 80(1): 34, 2013.
Bligh, E. et al., A Rapid Method of Total Lipid Extraction and Purification, Canadian Journal of Biochemistry and Physiology, 37(8): 911-917, 1959.
Blom, T. et al., FTY720 Stimulates 27-Hydroxycholesterol Production and Confers Atheroprotective Effects in Human Primary Macrophages, Circ. Res. 106: 720-729, 2010.
Boyum, A., Separation of white blood cells, Nature, 204: 793-794 1964.
Gan-Or. Z. et al., Differential effects of severe vs mild GBA mutations on Parkinson disease, Neurology, 84: 880-887, Mar. 3, 2015.
Ingemann, L. et al., Lysosomal storage diseases and the heat shock response: convergences and therapeutic opportunities, Journal of Lipid Research, 55: 2198-2210, May 16, 2014.
Mahalka, A. et al., Human heat shock protein 70 (Hsp70) as a peripheral membrane protein, Biochimica et Biophysica Acta, 1838: 1344-1361, Jan. 28, 2014.
McNeill et al., Amroxol improves lysosomal biochemistry in glucocerebrosidase mutation-linked Parkinson disease cells, Brain, 137: 1481-1495, Feb. 25, 2014.
Mu, T., et al., Chemical and biological approaches synergize to ameliorate protein-folding diseases, Cell, 134: 769-81, Sep. 5, 2008.
Sardi, S. et al., CNS expression of glucocerebrosidase corrects alpha-synuclein pathology and memory in a mouse model of Gaucher-related synucleinopathy, PNAS, 108(29): 12101-12106, Jul. 19, 2011.
Sardi, S. et al., Augmenting CNS glucocerebrosidase activity as a therapeutic strategy for parkinsonism and other Gaucher-related synucleinopathies, PNAS, 110(9): 3537-3542, Feb. 26, 2013.
Wang, S. et al,. ABCA1 and nascent HDL biogenesis, Biofactors 40(6): 547-554, Nov. 2014.
Witte, M. Et al., Ultrasensitive in situ visualization of active glucocerebrosidase molecules, Nature Chemical Biology, 6: 907-913, Oct. 31, 2010.
Xing. B. et al., Hsp70 plays an important role in high-fat diet induced gestational hyperglycemia in mice, J Physiol Biochem, 71: 649-658, Aug. 29, 2015.
Balwani, M. et al., Gaucher disease: when molecular testing and clinical presentation disagree, J Inhere Metab Dis, 34;789-793, 2011.
Schapira, A., Glucocerebrosidase and Parkinson disease: Recent advances, Molecular and Cellular Neuroscience, 66:37-42, 2015.
Liscic, R., Molecular basis of ALS and FTD: implications for translational studies, Arhiv za Hihijenu Rada i Toksikologiju, 66: 285-290, Dec. 1, 2015.
Rademakers et al., The Role of Tau (MAPT) in Frontotemporal Dementia and Related Tauopathies. Human Mutation, 24:277-295, 2004.
Gotzl, J. et al., Impaired Protein Degradation in FTLD and Related Disorders, Aging Res Rev. Dec.; 32:122-139, 2016.
Malik, B. et al., Co-induction of the heat shock response ameliorates disease progression in a mouse model of human spinal and bulbar muscular atrophy: implications for therapy, Brain, 136:926-43, 2013.
Custer, S. et al., Transgenic Mice Expressing Mutant Forms VCP/p97 Recapitulate the Full Spectrum of IBMPFD Including Degeneration in Muscle, Brain and Bone, Hum Mol Genet. 1;19(9):1741-55, 2010.
Ahmed, M. et al., Targeting Protein Homeostasis in Sporadic Inclusion Body Myositis, Sci. Tran Med; 8(331), 331ra41. Mar. 2016, 13 pages.
Ratti, A. et al., Physiological Functions and Pathobiology of TDP-43 and FUS/TLS Proteins, J Neurochem;138 Suppl 1:95-111, Aug. 2016.
Li, Q. et al., The cleavage pattern of TDP-43 determines its rate of clearance and cytotoxicity, Nature Communications 6:6183, Jan. 29, 2015.
Yoshiyama. Y. et al ., Frontotemporal Dementia and Tauopathy, Curr Neurol Neurosci Rep.; 1(5):413-21, Sep. 2001.
Tanida, I. et al., LC3 and Autophagy, Methods Mol Biol, 445, 77-88, 2008.
Lee, E. et al., Gains or losses: molecular mechanisms of TDP43-mediated neurodegeneration, Nat Rev Neurosci, 13:38-50, Nov. 30, 2011.
Tresse, E., et al., VCP/p97 is essential for maturation of ubiquitin-containing autophagosomes and this function is impaired by mutations that cause IBMPFD, Autophagy, 6: 217-227, 2010.
Higuchi, M. et al., Axonal Degeneration Induced by Targeted Expression of Mutant Human Tau in Oligodendrocytes of Transgenic Mice That Model Glial Tauopathies, J Neurosci., 25 (41): 9434-9443, Oct. 2005.
Jeong, H. et al., Brain Inflammation and Microglia: Facts and Misconceptions, Exp Neurobiol., 22(2): 59-67, Jun. 2013.
Monahan, Z. et al., Stress granules at the intersection of autophagy and ALS, Brain Res.1649(Pt B): 189-200, Oct. 15, 2016.
Ito, D. et al., RNA Binding Proteins and the Pathological Cascade in ALS/FTD Neurodegeneration, Sci Transl Med., 9(415): eeah5436, 2017.
Alberti, S. et al., Granulostasis: Protein Quality Control of RNP Granules, Front. Mol. Neurosci., 10:84, Mar. 27, 2017, 14 pages.
Fog, C. et al., The heat shock protein amplifier arimoclomol improves refolding, maturation and lysosomal activity of glucocerebrosidase, EBioMedicine, https://doi.org/10.1016/j.ebiom.2018.11.037.

\* cited by examiner (a)

(b)

HEAT SHOCK PROTEINS AND CHOLESTEROL HOMEOSTASIS

RELATED APPLICATIONS

This application is a National Phase application, filed under U.S.C. 371, of International Patent Application No. PCT/DK2017/050114, filed Apr. 10, 2017, which claims priority to, and the benefit of, Denmark Application No. PA 2016 70223, filed Apr. 13, 2016, the contents of each of which are incorporated by reference in their entirety.

TECHNICAL FIELD

The present invention relates to heat shock protein 70 (Hsp70) and bioactive agents that increases the intracellular concentration and/or activity of one or more heat shock proteins, including Hsp70, and their use in the treatment of diseases associated with dysregulation of cholesterol homeostasis, such as diseases associated with cholesterol efflux and/or cholesterol accumulation.

BACKGROUND

Cholesterol is an essential component of cell membranes, brain and nerve cells, and bile, which helps the body absorb fats and fat-soluble vitamins. The body uses cholesterol to make vitamin D and various hormones, such as estrogen, testosterone and cortisol. The body can produce all the cholesterol that it needs, but it also obtains cholesterol from food. To be able to circulate in blood, cholesterol and triglycerides are packaged with proteins and other substances to form lipoproteins. Lipoproteins include chylomicrons, very low density lipoproteins (VLDL), low-density lipoproteins (LDL), and high-density lipoproteins (HDL). Cholesterol transported by LDL is called LDL cholesterol, and cholesterol transported by HDL is called HDL cholesterol.

ATP-binding cassette transporter ABCA1 (member 1 of human transporter sub-family ABCA), also known as the cholesterol efflux regulatory protein (CERP) is a protein which in humans is encoded by the ABCA1 gene.

The membrane-associated protein encoded by this gene is a member of the super-family of ATP-binding cassette (ABC) transporters. ABC proteins transport various molecules across extra- and intracellular membranes. With cholesterol as its substrate, ABCA1 functions as a cholesterol efflux pump in the cellular lipid removal pathway, and is a major regulator of cellular cholesterol and phospholipid homeostasis.

ABCA1 mediates the efflux of cholesterol and phospholipids to lipid-poor apolipo-proteins (apo-A1 and apoE), which then form nascent high-density lipoproteins (HDL). It also mediates the transport of lipids between Golgi and cell membrane. It is expressed ubiquitously as a 220-kDa protein, and is present in higher quantities in tissues that shuttle or are involved in the turnover of lipids such as the liver, the small intestine and adipose tissue.

Downregulation of ABCA1 in senescent macrophages disrupts the cell's ability to remove cholesterol from its cytoplasm, leading the cells to promote the pathologic atherogenesis (blood vessel thickening/hardening) which play a central role in common age-associated diseases such as atherosclerosis and macular degeneration.

Mutations in ABCA1 and dysregulated cholesterol efflux have been associated with Tangier disease and familial high-density lipoprotein deficiency which features physiological deficiencies of HDL.

The molecular chaperones are found in all compartments of a cell where conformational rearrangements of proteins occur, and although protein synthesis is the major source of unfolded peptides in the cell, a challenge to the cell by high temperature or other stimuli that might render proteins structurally labile, and hence prone to unfolding and aggregation, is met with a specific cellular response involving the production of protective proteins. This response is a phenomenon observed in every cell type ranging from prokaryotes to eukaryotes and is referred to as the heat-shock- or stress-response. The proteins induced by this response are known as the heat shock proteins (HSPs), of which there exist several families.

A primary example of a family of chaperones is the Hsp70 proteins. This family has recently been implicated in other aspects of cellular homeostasis besides serving as a chaperone—most markedly through its anti-apoptotic features, its functions in immunity, and the apparent dependence of cancer cells on the upregulation of Hsp70. Furthermore, Hsp70 can serve a role in safeguarding lysosomal integrity.

SUMMARY

The present inventors have found that Hsp70 increases ABCA1 at the translational and transcriptional level. Also, Hsp70 is shown herewith to stimulate cholesterol efflux from macrophage foam cells, in particular efflux of cholesterol esters. This finding has potential in therapies involving at least ABCA1, cholesterol homeostasis and efflux, and provides a new means for restoring or enhancing cellular cholesterol efflux and increasing mature HDL.

It is an aspect to provide a bioactive agent that increases the intracellular concentration and/or activity of one or more heat shock proteins, including Hsp70, for use in the treatment of a disease associated with dysregulation of cholesterol homeostasis.

In one embodiment said bioactive agent that increases the intracellular concentration and/or activity of one or more heat shock proteins, including Hsp70, is Hsp70 protein, or a functional fragment or variant thereof.

In one embodiment said bioactive agent that increases the intracellular concentration and/or activity of one or more heat shock proteins, including Hsp70, is an inducer of Hsp70, such as a small molecule inducer of Hsp70, such as an inducer selected from arimoclomol, iroxanadine, bimoclomol, BGP-15, their stereoisomers and the acid addition salts thereof.

In one embodiment the disease associated with dysregulation of cholesterol homeostasis is a disease selected from the group consisting of: Smith-Lemli-Opitz Syndrome (SLOS), Antley-Bixler Syndrome, Hydrops-Ectopic Calcification-Moth-Eaten Skeletal Dysplasia (Greenberg dysplasia), Congenital Hemidysplasia with Ichthyosiform Nevus and Limb Defects Syndrome (CHILD), CK Syndrome, Conradi-Hünermann-Happle Syndrome (CPDX2, X-linked dominant chondrodysplasia punctate type 2), Lathosterolosis, Desmosterolosis, Mevalonate Kinase Deficiency (MKD) or (HIDS), Mevalonate Aciduria, atherosclerosis, Tangier disease and familial HDL deficiency.

for 3 days. Cholesterol efflux was performed for 12 h to complete medium in the presence or absence of rHSP70 (20 ug/ml). Lipids were analyzed by TLC. Pooled data from 8 blood donors from 8 independent experiments and three technical replicates, mean±SEM.

FIG. 2 Effect of rHsp70 on ABCA1 transcript and protein levels in primary human macrophage foam cells. Macrophages were loaded with acLDL followed by cholesterol efflux to complete medium in the absence or presence of rHSP70. (a) The ABCA1 mRNA levels were measured by qRT-PCR. Data are mean±SEM, n=6 blood donors with triplicate measurements. (b) Cells were harvested and equal amounts of protein separated by SDS-PAGE and analyzed by Western blotting using a polyclonal anti-ABCA1 antibody. ProAct staining was used as a loading control. Data are mean±SEM, n=7 blood donors.

Figure 3:
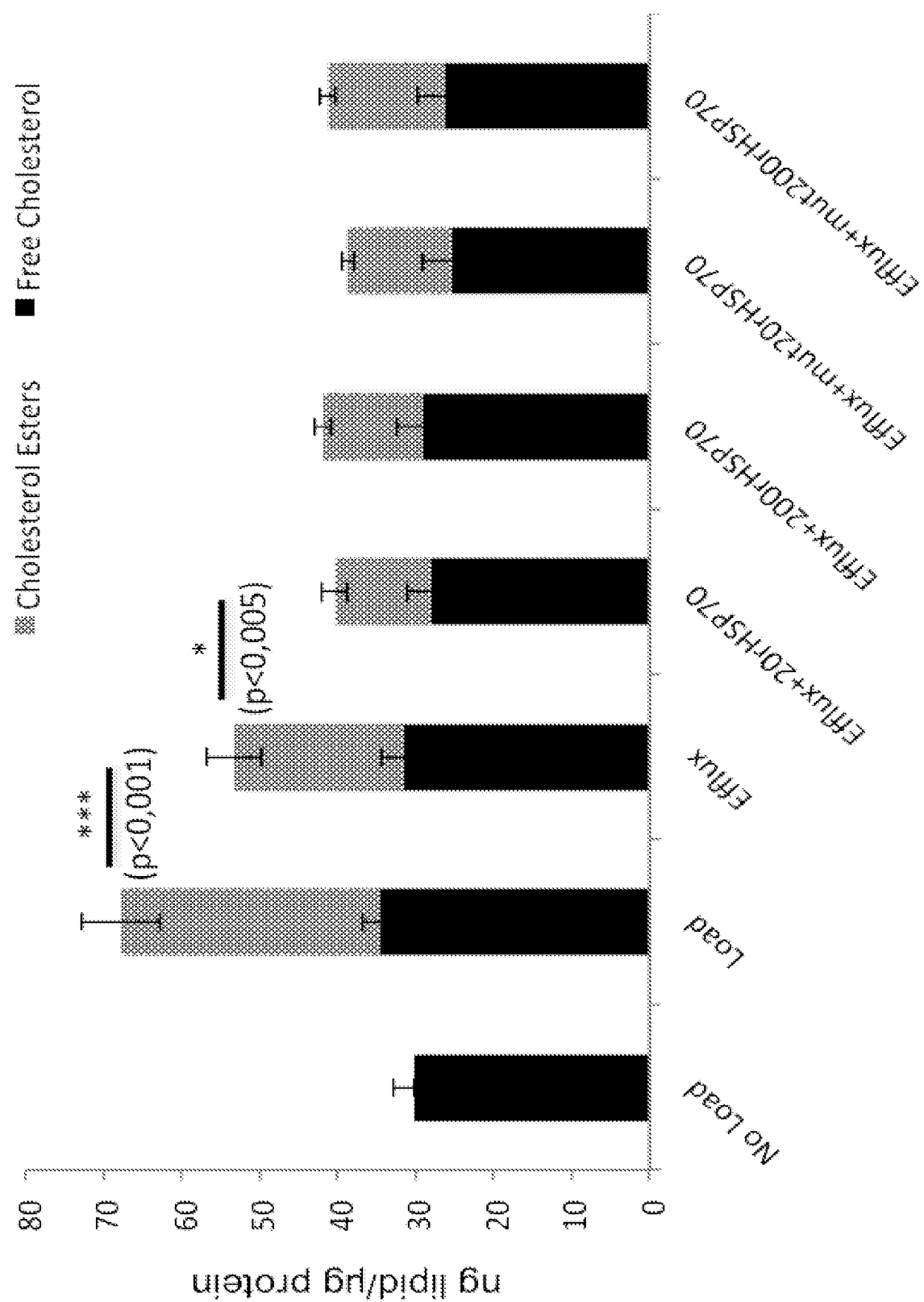

FIG. 3 The effect of rHsp70 dose and BMP binding on cholesterol efflux from primary human macrophage foam cells. Macrophages were loaded with acLDL followed by cholesterol efflux to complete medium in the absence or presence of rHSP70 as in FIG. 1. Either wild-type or W90F mutant (mut) rHsp70 was employed at the final concentrations of 20 or 200 µg/mL Pooled data from 2 individual donors with 3 technical replicates, mean±SEM.

Figure 4:
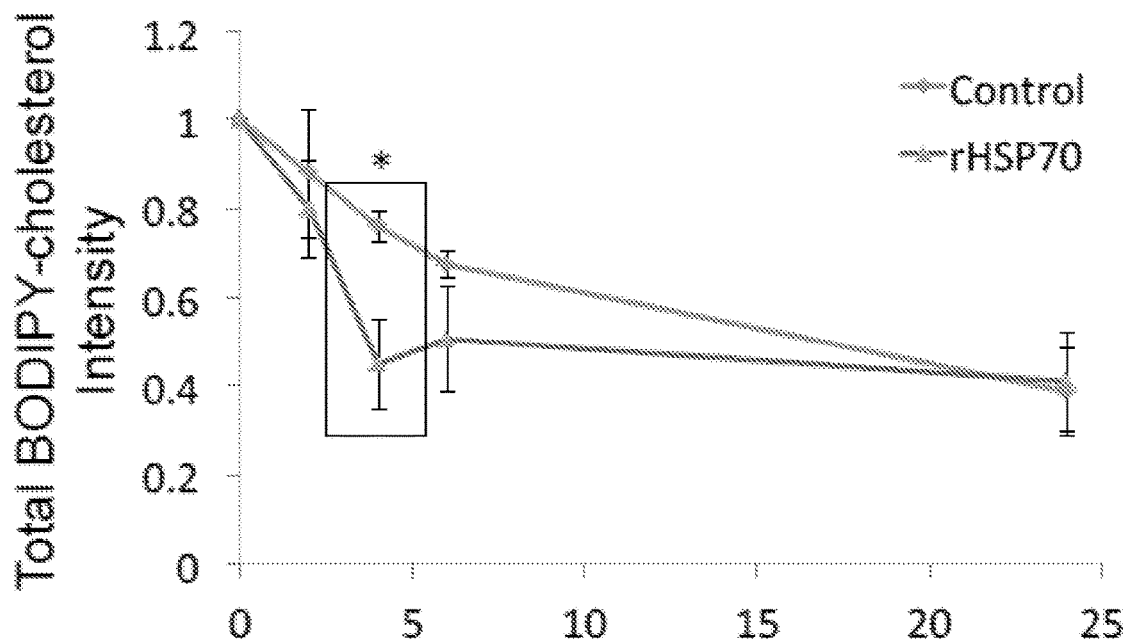
Figure 4:
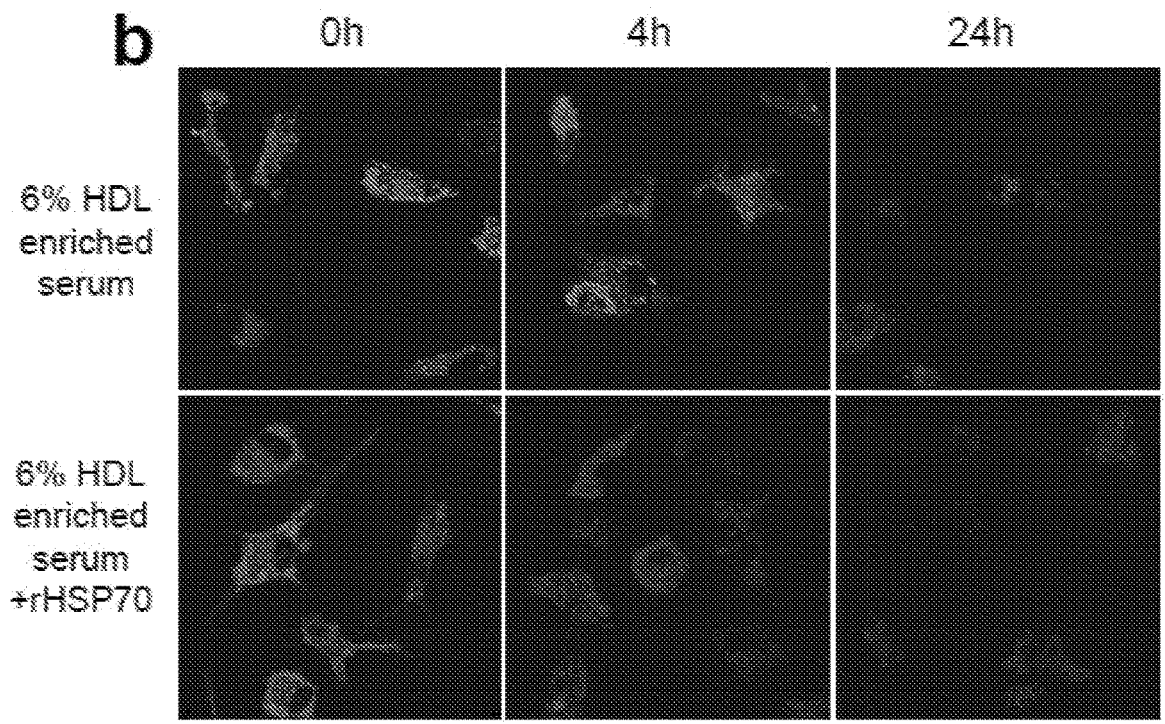

FIG. 4 rHSP70 speeds up BODIPY-cholesterol efflux from primary murine macrophage foam cells. Primary murine bone marrow macrophage foam cells were incubated with BODIPYcholesteryl linoleate-LDL particles. Cholesterol efflux was performed for 24 h to 6% HDL enriched serum in the presence or absence of rHSP70. Images were taken using Leica SP8 scanning confocal microscope at the indicated time points. (a) Total cell BODIPY-cholesterol intensity changes were calculated using ImageJ and data normalized to 0 h. (b) Representative images of BODIPY-cholesterol intensity changes over time. n=60-100 cells/condition. *: $p<0.05$.

Figure 5:
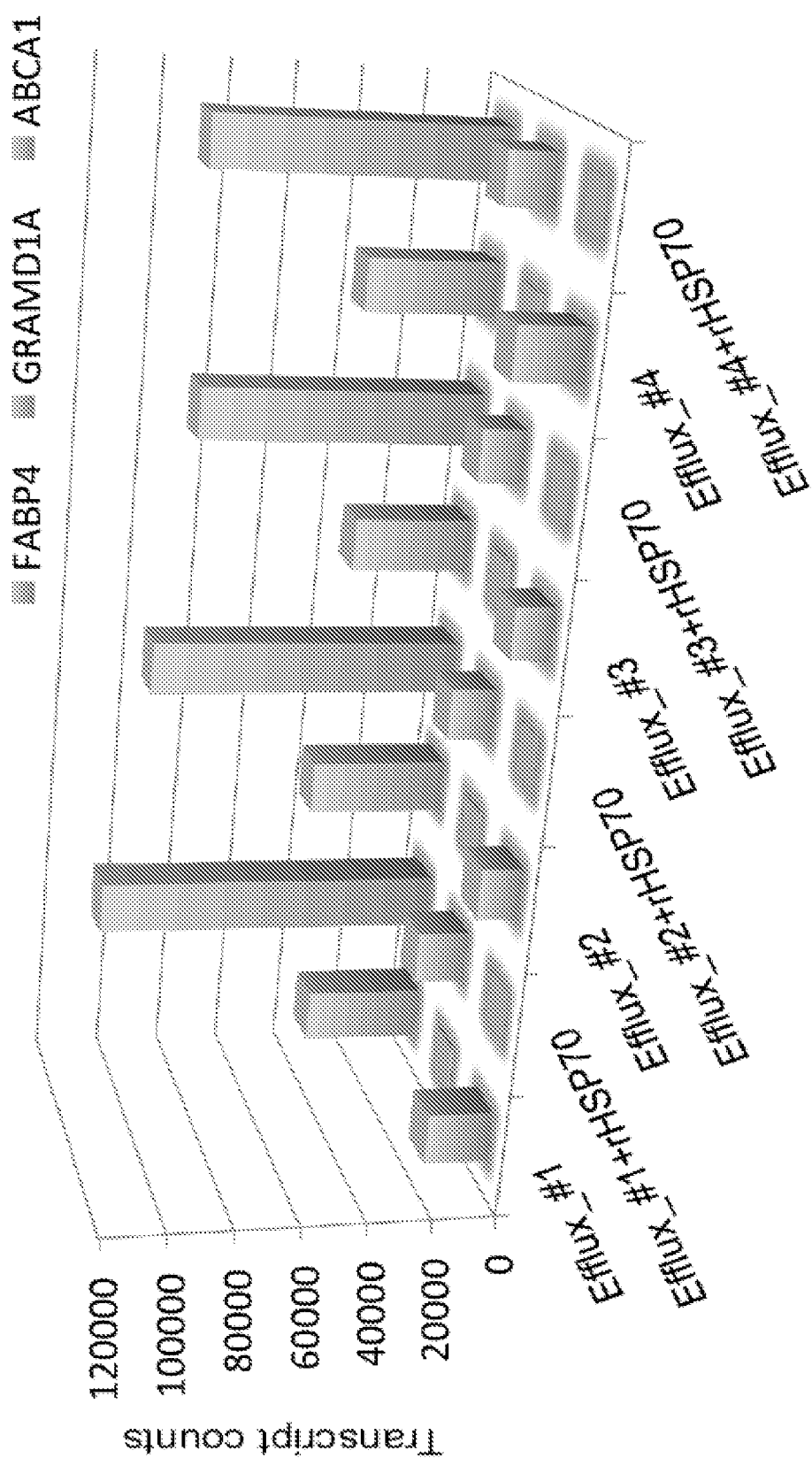

FIG. 5 The effect of rHSP70 on transcript levels of selected LXR targets in primary human macrophage foam cells. Macrophage foam cells from 4 individual blood donors were incubated −/+rHSP70 during cholesterol efflux and RNAs were extracted. RNA sequencing was performed by Illumina NextSeq sequencer. RNASeq results were analysed using "Gene Set Enrichment Analysis". Selected LXR pathway targets modulated by rHSP70 administration were plotted against their transcript count numbers. Front row: FABP4; middle row: GRAMD1A; back row: ABCA1.

Figure 6A:
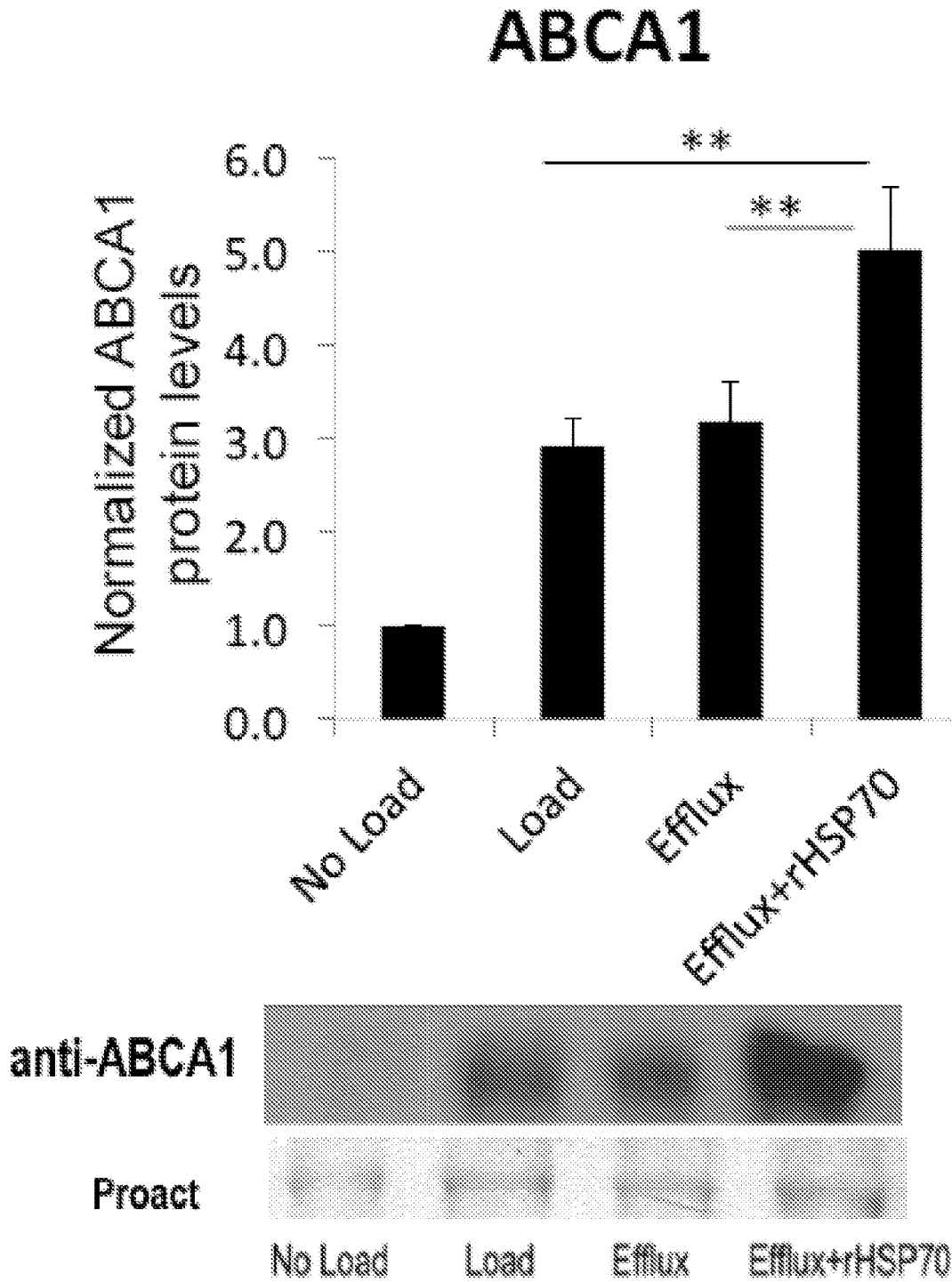
Figure 6B:
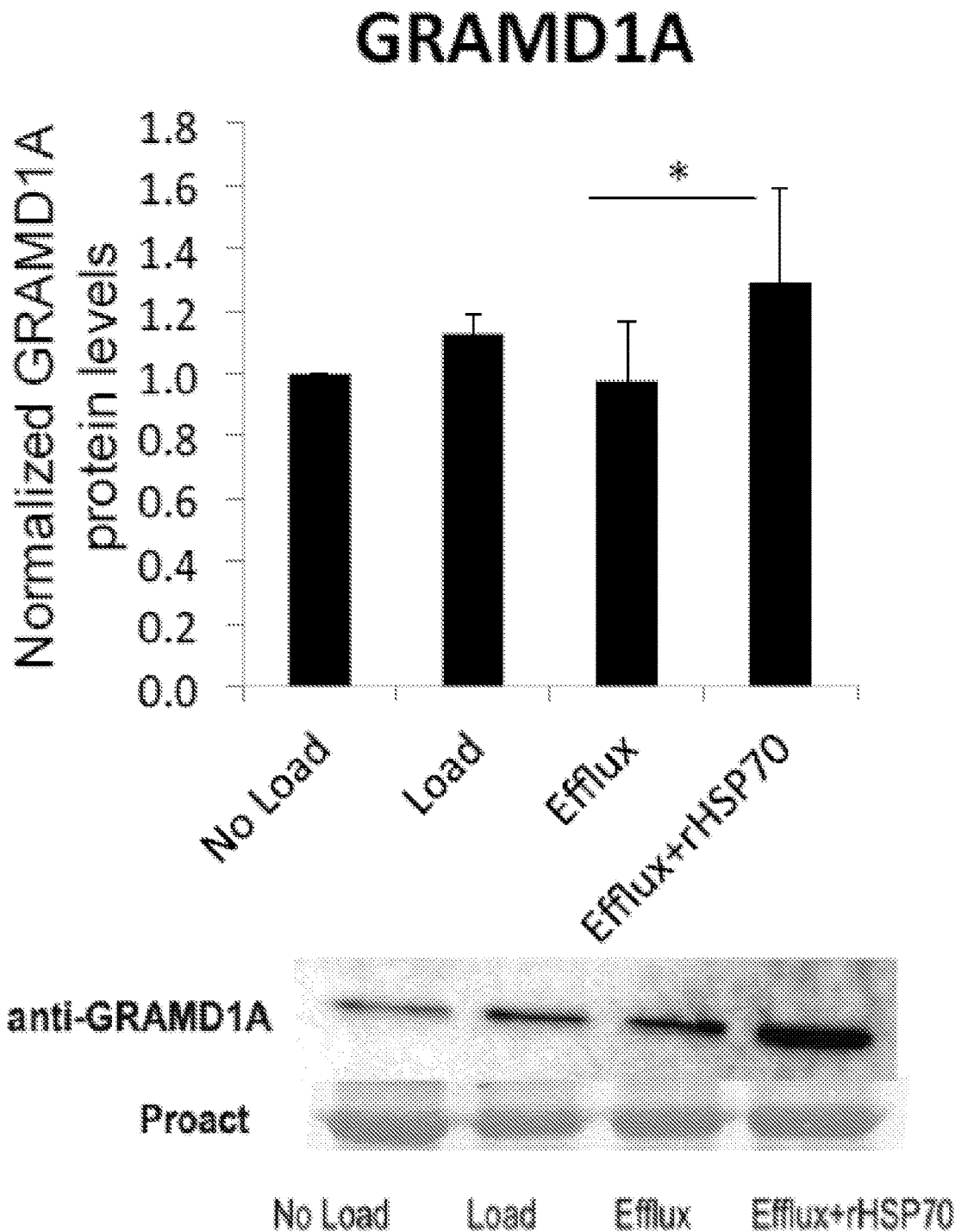
Figure 6C:
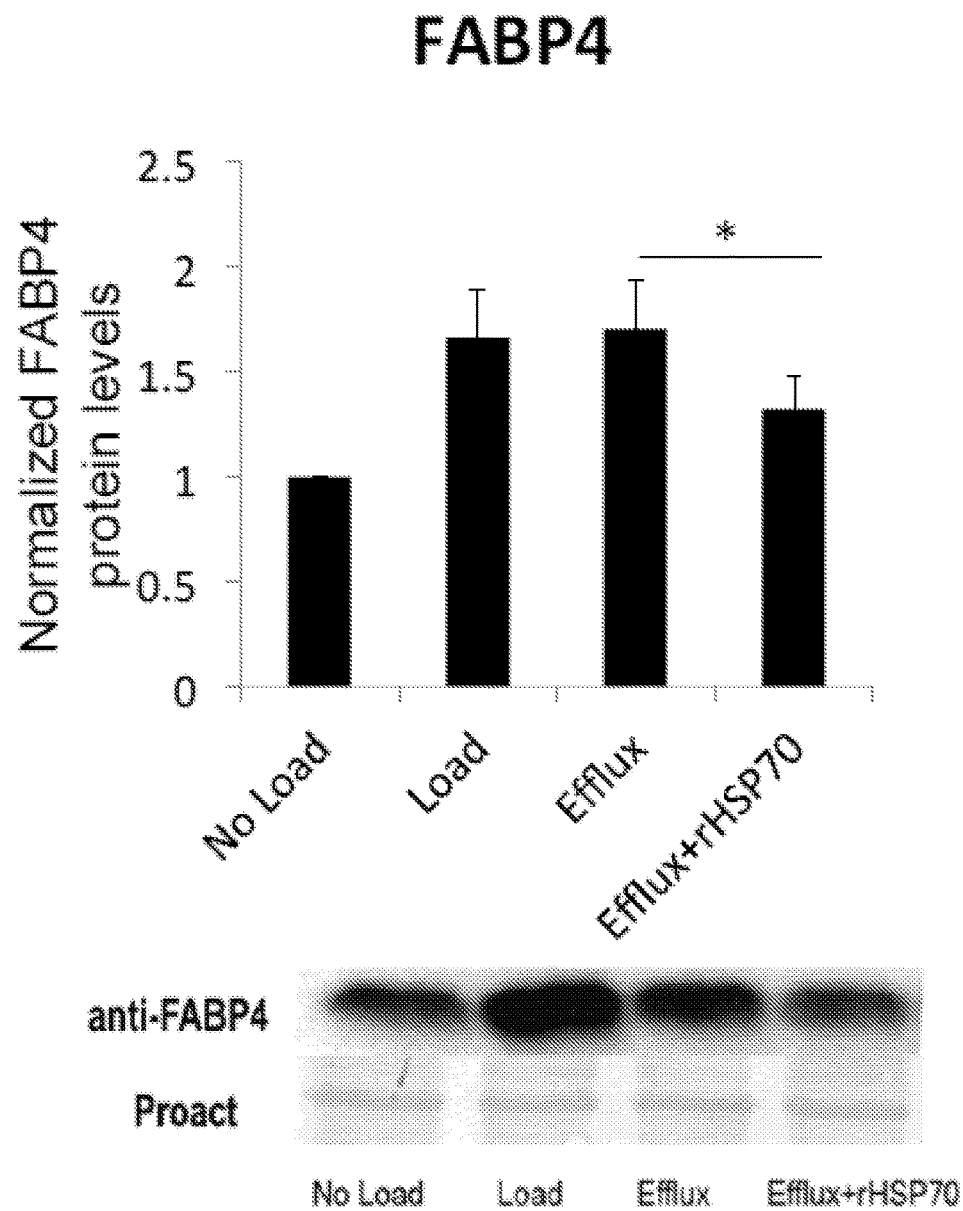

FIG. 6 The effect of rHSP70 on protein levels of selected LXR targets in primary human macrophage foam cells. Cells (as described for FIG. 5) were harvested and equal amounts of protein separated by SDS-PAGE and analyzed by Western blotting. Data are mean±SEM, n=7 blood donors. *: $p<0.05$; **: $p<0.01$. (a) ABCA1, (b) GRAMD1A, (c) FABP4.

DETAILED DESCRIPTION

The effect of inducing the heat shock response, including the effect on heat shock proteins, specifically Hsp70, on ABCA1 and cholesterol efflux has potential in therapies involving at least ABCA1, cholesterol homeostasis and/or efflux, and foam cells.

It is thus an aspect of the present invention to provide a bioactive agent as defined herein that increases the intracellular concentration (or levels) and/or activity of one or more heat shock proteins, including Hsp70, for use in the treatment of a disease associated with dysregulation of cholesterol homeostasis.

In one embodiment there is provided use of a bioactive agent as defined herein that increases the intracellular concentration and/or activity of one or more heat shock proteins, including Hsp70, for the manufacture of a medicament for the treatment of a disease associated with dysregulation of cholesterol homeostasis.

In one embodiment there is provided a method of treating a disease associated with dysregulation of cholesterol homeostasis, said method comprising one or more steps of administering a bioactive agent as defined herein that increases the intracellular concentration and/or activity of one or more heat shock proteins, including Hsp70, to an individual in need thereof.

The term "Individual" or "subject" refers to vertebrates, in particular a member of a mammalian species, preferably primates including humans. In a preferred embodiment, an individual as used herein is a human being, male or female, of any age.

An "individual in need thereof" refers to an individual who may benefit from the present invention. In one embodiment, said individual in need thereof is a diseased individual, wherein said disease is associated with dysregulation of cholesterol homeostasis and/or cholesterol efflux such as from macrophage foam cells.

In one embodiment, said treatment may be prophylactic, curative or ameliorating. In one particular embodiment, said treatment is prophylactic. In another embodiment, said treatment is curative. In a further embodiment, said treatment is ameliorating.

The bioactive agents that increases the intracellular concentration and/or activity of one or more heat shock proteins, including Hsp70, are defined in detail herein below, and encompasses Hsp70 protein per se and inducers of heat shock proteins including Hsp70.

The diseases associated with dysregulation of cholesterol homeostasis are defined in detail herein below, and encompasses diseases associated with cholesterol accumulation, diseases of cholesterol metabolism, disease of cholesterol biosynthesis and a disease associated with the cholesterol transporter ABCA1 and/or foam cells, such as Tangier disease, familial HDL deficiency and atherosclerosis.

The Molecular Chaperones Having spent vast amounts of energy upon first transcribing and then translating the genetic code of DNA, the cell has finally produced a polypeptide, whose function presumably is required at this point in the cell's life. However, some final obstacles has to be overcome in order to achieve a fully functional protein—one of these being correct folding of this nascent polypeptide chain. The evolutionary imperatives of achieving correct folding are obvious—not only would it be a terrible waste of energy to have synthesized a peptide without the proper conformation and hence function, but also the aggregation of such proteins in the cellular lumen could prove detrimental to the cell. This aggregation is in fact a very likely outcome, considering the intracellular environment of high protein concentration, so it comes as no surprise that a complicated and sophisticated machinery of proteins exists to assist protein folding, allowing the functional state of proteins to be maintained under such conditions. These proteins are collectively called molecular chaperones, because, like their human counterparts, they prevent unwanted interactions between their immature clients.

The molecular chaperones are found in all compartments of a cell where conformational rearrangements of proteins occur, and although protein synthesis is the major source of unfolded peptides in the cell, a challenge to the cell by high temperature or other stimuli that might render proteins structurally labile, and hence prone to unfolding and aggregation, is met with a specific cellular response involving the production of protective proteins. This response is a phenomenon observed in every cell type ranging from prokaryotes to eukaryotes and is referred to as the heat-shock- or stress-response. The proteins induced by this response are known as the heat shock proteins (HSPs), of which there exist several families. These families are composed of both sequentially, structurally and functionally related proteins, whereas chaperones from different families can differ markedly both in structure as well as cellular function. A primary example of a family of chaperones are the Hsp70 proteins, which constitute the central part of an ubiquitous chaperone system present in most compartments of eukaryotic cells, in eubacteria, and in many archae. This family has recently been implicated in other aspects of cellular homeostasis besides serving as a chaperone—most markedly through its anti-apoptotic features, its functions in immunity, and the apparent dependence of cancer cells on the upregulation of Hsp70.

The Heat Shock Protein 70 Family

Hsp70 proteins are involved in a wide range of cellular processes including protein folding and degradation of unstable cellular proteins as well as serving other cytoprotective roles. The common function of Hsp70 in these processes appears to be the binding of short hydrophobic segments in partially folded polypeptides, thereby facilitating proper folding and preventing aggregation. In eukaryotes, Hsp70 chaperones interact in vivo with different classes of proteins that serve to regulate critical steps of their functional cycle; amongst these the J-domain family protein Hsp40. Furthermore, additional partner proteins have been identified, some of which are linking Hsp70 to other chaperone systems such as the Hsp90 system.

Members of the Human Hsp70 Family

Some of the important functions attributed to the molecular chaperones include import of proteins into cellular compartments, folding of proteins in the cytosol, endoplasmic reticulum and mitochondria, prevention of protein aggregation and refolding of misfolded proteins. At present the human Hsp70 family includes 10 members encoded by different genes, and this section is meant to provide an overview of these family members with respect to function, expression patterns and homology. Some confusion exists about the nomenclature of the different human Hsp70 family members, although a set of general guidelines has been set forth by Tavaria et al., which provides a logical link between locus names, genes and proteins. However, as there still exists some interspecies confusion, the Hsp70 genes and proteins are referred to herein by their locus name. The name Hsp70 may refer to the two inducible Hsp70 family members with loci names HSPA1A and HSPA1B or to the whole Hsp70 family in general as evident from the consensus of the text.

HspA1A and HspA1B

The genes transcribed from the loci HSPA1A and HSPA1B are the two heat/stress-inducible Hsp70-genes and the majority of the literature concerning human Hsp70 refers to the proteins encoded by these two genes. The genes give rise to proteins consisting of 641 amino acids, having 99% homology to each other and were the first human Hsp70 family members to be cloned and characterized. The genes are linked in the MHC-class III complex at 6p21.3, are intron-less and with promoter regions containing HSEs, enabling them to bind HSFs and induce transcription in response to a variety of cellular assaults.

HspA1L and HspA2

Two Hsp70 family members have been termed "chauvinist genes" because male germ cells favor their expression with strong prejudice. The hspA1L gene is a constitutively expressed intron-less Hsp70 family member located 4 kb telomeric to the HSPA1A locus in the same MHC-class III complex on chromosome 6. It is expressed in low amounts both before and after heat shock but with the expression pattern favoring the testes in mouse, rat and humans with the 641 amino acids (aa) protein being 90% homologous to HspA1A. The hspA2 gene was first isolated from a mouse genomic library and has later been shown to be constitutively expressed albeit in low levels in various tissues in the human body including skeletal muscle, ovary, small intestine, colon, brain, placenta and the kidneys, but highly expressed in testis. Its expression, or rather lack thereof, has been connected with abnormal human spermatogenesis and male hspA2$^{(-/-)}$ mice are sterile. The gene is located on chromosome 14, giving rise to a 639 aa protein with 84% homology to HspA1A, although the exact location is subject to discussion as two papers have presented different loci positions—14q24.1 vs. 14q22.

HspA6 and HspA7

The hspA6 and hspA7 genes are heat inducible members of the Hsp70 family with no apparent counterparts in mice. They contain HSEs in their promoter-sites and the genes are intron-less. They are co-localized on chromosome 1 and are 94% homologous to each other in the nucleotide sequence. However, only HspA6 is functional as the hspA7 gene harbors a single nucleotide insertion generating a premature stop codon at +1324. The HspA6 protein is 643 aa long and shows 77% homology to HspA1A and HspA1B.

HspA5 and HspA9

The hspA5 and hspA9 genes are the two compartment-specific members of the Hsp70 family. The 655 aa HspA5 protein is located in the endoplasmic reticulum (ER) and facilitates folding and transport of newly synthesized proteins in this compartment. The protein is 64% homologous to HspA1A, the gene being located at 9q34. The 679 aa HspA9 protein is located in the mitochondria where it assists in folding of proteins after their transport across the mitochondrial membrane. HspA9 is located at 5q31.1, the protein being 52% homologous to HspA1A.

HspA8

The cognate Hsp70 member known as Hsc70 is encoded by a gene named hspA8 at 11q24, giving rise to a 646 aa protein with 86% homology to HspA1A, and is constitutively expressed in all tissues and cell lines. The protein is analogous to Hsp70 in its cellular functions, providing the required chaperoning under normal circum-stances, but has also been ascribed a role in the un-coating of clathrin-coated vesicles as well as in chaperone-mediated autophagy.

HspA3 and HspA4

These will not be discussed here, as there is doubt as to whether HSPA3 exists at all and since HSPA4 is most likely a member of the Hsp110 family and nothing is known about it so far, except for its chromosomal location at 5q31.1-2.

TABLE 1

List of the Human Hsp70 Gene Family. The genes are listed according to locus name, names used herein, chromosomal location (position), amino acid homology to HspA1A as well as alternative names often seen in the literature.

| Locus | Name Used herein, Gene/Protein | Position | % aa Homology to HSPA1A | Alternative Names |
|---|---|---|---|---|
| HSPA1A | hspA1A/HspA1A (Hsp70) | 6p23.1 | 100 | Hsp70; Hsp72; Hsp70-1 |
| HSPA1B | hspA1B/HspA1B (Hsp70) | 6p23.1 | 99 | Hsp70; Hsp72; Hsp70-2 |
| HSPA1L | hspA1L/HspA1L | 6p23.1 | 90 | Hsp70-Hom; Hsp70t |
| HSPA2 | hspA2/HspA2 | 14q24.1 | 84 | Hsp70-3 |
| HSPA4 | hspA4/HspA4 | 5q31.1 | 31 | Hsp70RY; APG-2 |
| HSPA5 | hspA5/HspA5 | 9q34 | 64 | BiP; GRP78 |
| HSPA6 | hspA6/HspA6 | 1q | 84 | Hsp70-6; Hsp70B' |
| HSPA7 | hspA7/HspA7 | 1q | — | Hsp70-7; Hsp70B |
| HSPA8 | hspA8/HspA8 (Hsc70) | 11q24 | 86 | Hsc70; Hsp73 |
| HSPA9 | hspA9/HspA9 | 5q31.1 | 52 | GRP75; PBP74; mtHsp75; mortalin; mot-2 |

Bioactive Agent

A "Bioactive agent" (i.e., biologically active substance/agent) is any agent, drug, substance, compound, composition of matter or mixture which provides some pharmacologic, often beneficial, effect that can be demonstrated in vivo or in vitro. As used herein, this term further includes any physiologically or pharmacologically active substance that produces a localized or systemic effect in an individual. Further examples of bioactive agents include, but are not limited to, agents comprising or consisting of an oligosaccharide, a polysaccharide, an optionally glycosylated peptide, an optionally glycosylated polypeptide, a nucleic acid, an oligonucleotide, a polynucleotide, a lipid, a fatty acid, a fatty acid ester and secondary metabolites.

A bioactive agent as defined herein increases the intracellular concentration and/or activity of one or more heat shock proteins, including Hsp70. In one embodiment said bioactive agent is selected from:

Hsp70 protein, or a functional fragment or variant thereof,
Inducers of heat shock proteins including Hsp70, such as
  Hsp70 inducers
    small molecule inducers of heat shock proteins, including Hsp70;
      hydroxylamine derivatives, e.g. bimoclomol, arimoclomol, iroxanadine and BGP-15
    Membrane fluidizers, such as benzyl alcohol
    Sub-lethal heat-therapy 42° C.) or hyperthermia
    Certain anti-inflammatory and anti-neoplastic drugs
    Cellular stressors;
      Reactive oxygen species (ROS); Adrenalin, noradrenalin; UV light; Radiation therapy.

A bioactive agent as defined herein is thus any agent, chemical or compound that increases the intracellular concentration (or level) and/or activity of one or more heat shock proteins including Hsp70; and includes Hsp70 itself, or a functional fragment or variant thereof, and any Hsp70 inducer known to the skilled person.

A bioactive agent that increases the intracellular concentration and/or activity of one or more heat shock proteins, including Hsp70, and a bioactive agent that increases the intracellular concentration and/or activity of Hsp70, is used interchangeably with 'Hsp70 inducer' herein.

An Hsp70 inducer can amplify Hsp70 gene expression and protein expression with or without a concomitant stress. A direct Hsp70 inducer is a compound that can by itself amplify Hsp70 gene expression and protein expression without a concomitant stress. An indirect Hsp70 inducer, or an Hsp70 co-inducer, is a compound that cannot amplify Hsp70 gene expression and protein expression without a concomitant (mild) stress, but the stress-induced increase in Hsp70 levels is further elevated or enhanced by their presence.

It follows that a bioactive agent may increase the intracellular concentration and/or activity of Hsp70 either directly or indirectly.

In one embodiment, the bioactive agent is Hsp70, or a functional fragment or variant thereof.

In another embodiment, the bioactive agent is an inducer of heat shock proteins, including Hsp70.

In one embodiment the inducer of heat shock proteins, including Hsp70, is an inducer of one or more of Hsp70, Hsp40, Hsp72 and Hsp90. In one embodiment the inducer of heat shock proteins is an inducer of at least Hsp70. In one embodiment the inducer of heat shock proteins is an inducer of Hsp70.

Reference to an inducer of Hsp70, or inducing Hsp70, implies that at least Hsp70 is induced, and does not exclude co-induction of other proteins and effectors such as other heat shock proteins. An inducer of Hsp70 refers equally to Hsp70 inducers and co-inducers, and direct and indirect Hsp70 inducers.

In one embodiment, the bioactive agent comprises a combination of Hsp70, or a functional fragment or variant thereof, and an inducer of heat shock proteins including Hsp70.

In one embodiment, the bioactive agent increases ABCA1 at the translational and transcriptional level. In another embodiment, the bioactive agent stimulates cholesterol efflux from macrophage foam cells, in particular efflux of cholesterol esters.

Heat Shock Protein 70

It is an aspect to provide Hsp70, or a functional fragment or variant thereof, for use in treating a disease associated with dysregulation of cholesterol homeostasis.

In one embodiment there is provided use of Hsp70, or a functional fragment or variant thereof, for the manufacture of a medicament for the treatment of a disease associated with dysregulation of cholesterol homeostasis.

In one embodiment there is provided a method of treating a disease associated with dysregulation of cholesterol homeostasis, said method comprising one or more steps of administering Hsp70, or a functional fragment or variant thereof, to an individual in need thereof.

It is understood that Hsp70, or a functional fragment or variant thereof, as defined herein can be any natural or synthetic product, and may be produced by any conventional technique known to the person skilled in the art.

In one embodiment, Hsp70, or a functional fragment or variant thereof, is purified from a natural source. Said natural source may be any plant, animal or bacteria which expresses, or may be induced to express, Hsp70 in a form suitable for administering to an individual in need thereof.

In a particular embodiment, Hsp70, or a functional fragment or variant thereof, is made synthetically. It follows that Hsp70, or a functional fragment or variant thereof, in one embodiment is a recombinant protein made by conventional techniques and as such is denoted rHsp70.

The Hsp70 as defined herein, synthetic or natural, in one embodiment has a sequence which is derived from any suitable species of plant, animal or bacteria. In one embodiment, said rHsp70 is derived from a mammal. Said mammal is in one embodiment selected form the group consisting of human (Homo sapiens), mouse (Mus musculus), cow, dog, rat, ferret, pig, sheep, and monkey. In another embodiment, said rHsp70 is derived from bacteria.

Hsp70 is characterized in part by having a very high degree of interspecies sequence conservation, thus possibly allowing for Hsp70 derived from one species to be used in another species without eliciting a harmful immune response.

In one particular embodiment, said rHsp70 has a sequence derived from human Hsp70.

In one particular embodiment, said rHsp70 has a sequence derived from more than one species. Said Hsp70, or a functional fragment or variant thereof, may thus in one embodiment be a chimera.

In one embodiment Hsp70 is meant to denote any of the two inducible Hsp70 family members with loci names HSPA1A and HSPA1B.

In one embodiment said Hsp70 is selected from HSPA1A (SEQ ID NOs:1 and 2) and HSPA1B (SEQ ID NOs:4 and 5), or a functional fragment or variant thereof. In SEQ ID NO:2 the initiator methionine (M at position 1) of SEQ ID NO:1 is removed. In SEQ ID NO:5 the initiator methionine (M at position 1) of SEQ ID NO:4 is removed. In vivo this occurs by post-translational processing.

In one embodiment, the Hsp70 is selected from any one of SEQ ID NO:s 1, 2, 4 and 5, or functional fragments or variants thereof, including any naturally occurring variants thereof, such as variants derived from molecule processing and/or amino acid modifications (including any acetylation, phosphorylation and methylation).

In one embodiment, the Hsp70 protein has 100% identity to wild-type Hsp70 protein. In another embodiment, the Hsp70 protein has less than 100% identity to the wild-type Hsp70 protein, such as 99.9 to 95% identity, for example 95 to 90% identity, such as 90 to 85% identity, for example 85 to 80% identity, such as 80 to 75% identity, for example 75 to 60% identity to the wild-type protein. Regardless of the degree of identity, any fragment or variant of Hsp70 that retains its relevant biological effects is encompassed herewith.

In one embodiment said variant of Hsp70 has 99.9 to 99% identity, for example 99 to 98% identity, such as 98 to 97% identity, for example 97 to 96% identity, such as 96 to 95% identity, for example 95 to 94% identity, such as 94 to 93% identity, for example 93 to 92% identity, such as 92 to 91% identity, for example 91 to 90% identity, such as 90 to 85% identity, for example 85 to 80% identity, such as 80 to 75% identity, for example 75 to 70% identity, such as 70 to 65% identity, for example 65 to 60% identity to Hsp70 selected from HSPA1A (SEQ ID NOs:1 and 2) and HSPA1B (SEQ ID NOs: 4 and 5), or a fragment thereof.

In one embodiment, the bioactive agent is Hsp70. In one embodiment, said Hsp70 is full length Hsp70. In one embodiment said Hsp70 is HSPA1A, or a functional fragment or variant thereof. In one embodiment said Hsp70 is SEQ ID NO:1 or 2, or a functional fragment or variant thereof.

It is also an embodiment to provide a functional fragment or variant of Hsp70. As defined herein, a functional fragment or variant is any fragment or variant of Hsp70 which retains the capability of one or more of:
  i) stimulating cholesterol efflux from macrophages, such as lipid laden macrophages, such as foam cells,
  ii) stimulating the decrease of cholesterol esters in macrophages, such as lipid laden macrophages, such as foam cells,
  iii) facilitating cholesterol reduction during macrophage foam cell reversal,
  iv) reducing intracellular cholesterol in macrophages,
  v) increasing or stimulating ABCA1 levels and/or activity,
  vi) increasing or stimulating ABCA1-protein levels and/or activity, and/or
  vii) increasing or stimulating ABCA1-mRNA levels and/or activity.

In one embodiment, the bioactive agent is a functional fragment or variant of Hsp70.

In one embodiment, the bioactive agent is a functional fragment or variant of Hsp70, in which Hsp70 is modified by one or more deletion(s), addition(s) or substitution(s) of the wild type Hsp70.

In one embodiment, the bioactive agent is a naturally occurring variant of Hsp70, or a fragment of a naturally occurring variant of Hsp70.

In one embodiment a variant of Hsp70 comprises one or more of D→A at position 10, E→D at position 110, D→A at position 199, K→R at position 561, N-acetylalanine at position 2, N6-acetyllysine at position 108, N6-acetyllysine at position 246, N6-acetyllysine at position 348, N6,N6,N6-trimethyllysine at position 561, phosphoserine at position 631, phosphoserine at position 633 and phosphothreonine at position 636. In one embodiment a naturally occurring variant of Hsp70 is Isoform 1 wherein amino acids of position 96-150 are missing (PODMV8-2).

In one embodiment, a functional fragment or variant of Hsp70 is a variant of Hsp70 in which one or more amino acids has been substituted (or mutated). Said substitution(s) comprises equivalent or conservative substitution(s), or a non-equivalent or non-conservative substitution(s). The term Hsp70 and variants thereof also embraces post-translational modifications introduced by chemical or enzyme-catalyzed reactions, as are known in the art, and chemical modifications such as ubiquitination, labeling, pegylation, glycosylation, amidation, alkylation and esterification. In one embodiment said Hsp70 has been post-translationally modified, including including acetylation, phosphorylation and methylation at any position.

In one embodiment 0.1 to 1% of the amino acid residues of wild type Hsp70 has been substituted, such as 1 to 2%, for example 2 to 3%, such as 3 to 4%, for example 4 to 5%, such as 5 to 10%, for example 10 to 15%, such as 15 to 20%, for example 20 to 30%, such as 30 to 40%, for example 40 to 50%, such as 50 to 60%, for example 60 to 70%, such as 70 to 80%, for example 80 to 90%, such as 90 to 100% amino acid residues.

In one embodiment 1-2, 2-3, 3-4, 4-5 of the amino acid residues of wild type Hsp70 has been substituted, such as 5 to 10, for example 10 to 15, such as 15 to 20, for example 20 to 30, such as 30 to 40, for example 40 to 50, such as 50 to 75, for example 75 to 100, such as 100 to 150, for example 150 to 200, such as 200 to 300, for example 300 to 400, such as 400 to 500 amino acid residues.

In one embodiment, the Hsp70 or functional fragment or variant of Hsp70 is a fusion protein. In one embodiment, said Hsp70 or functional fragment or variant of Hsp70 is fused to a tag.

An "equivalent amino acid residue" refers to an amino acid residue capable of replacing another amino acid residue in a polypeptide without substantially altering the structure and/or functionality of the polypeptide. Equivalent amino acids thus have similar properties such as bulkiness of the side-chain, side chain polarity (polar or non-polar), hydrophobicity (hydrophobic or hydrophilic), pH (acidic, neutral or basic) and side chain organization of carbon molecules (aromatic/aliphatic). As such, "equivalent amino acid residues" can be regarded as "conservative amino acid substitutions".

The classification of equivalent amino acids refers in one embodiment to the following classes: 1) HRK, 2) DENQ, 3) C, 4) STPAG, 5) MILV and 6) FYW Within the meaning of the term "equivalent amino acid substitution" as applied herein, one amino acid may be substituted for another, in one embodiment, within the groups of amino acids indicated herein below:
i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphor-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

The wild type Hsp70 protein has a total length of 641 amino acids (640 amino acids after removal of initiator methionine at position 1). A fragment of Hsp70 is in one embodiment meant to comprise any fragment with a total length of less than the wild type protein, such as less than 625 amino acids, for example less than 600 amino acids, such as less than 575 amino acids, for example less than 550 amino acids, such as less than 525 amino acids, for example less than 500 amino acids, such as less than 475 amino acids, for example less than 450 amino acids, such as less than 425 amino acids, for example less than 400 amino acids, such as less than 375 amino acids, for example less than 350 amino acids, such as less than 325 amino acids, for example less than 300 amino acids, such as less than 275 amino acids, for example less than 250 amino acids, such as less than 225 amino acids, for example less than 200 amino acids, such as less than 175 amino acids, for example less than 150 amino acids, such as less than 125 amino acids, for example less than 100 amino acids, such as less than 75 amino acids, for example less than 50 amino acids, such as less than 25 amino acids derived from Hsp70.

In another embodiment a fragment of Hsp70 is meant to comprise any fragment with a total length of more than 10 amino acids, such as more than 25 amino acids, for example more than 50 amino acids, such as more than 75 amino acids, for example more than 100 amino acids, such as more than 125 amino acids, for example more than 150 amino acids, such as more than 175 amino acids, for example more than 200 amino acids, such as more than 225 amino acids, for example more than 250 amino acids, such as more than 275 amino acids, for example more than 300 amino acids, such as more than 325 amino acids, for example more than 350 amino acids, such as more than 375 amino acids, for example more than 400 amino acids, such as more than 425 amino acids, for example more than 450 amino acids, such as more than 475 amino acids, for example more than 500 amino acids, such as more than 525 amino acids, for example more than 550 amino acids, such as more than 575 amino acids, for example more than 600 amino acids, such as more than 625 amino acids derived from Hsp70.

In one embodiment the total length of the fragment of Hsp70 is 5 to 25 amino acids, such as 25 to 50 amino acids, for example 50 to 75 amino acids, such as 75 to 100 amino acids, for example 100 to 125 amino acids, such as 125 to 150 amino acids, for example 150 to 175 amino acids, such as 175 to 200 amino acids, for example 200 to 225 amino acids, such as 225 to 250 amino acids, for example 250 to 275 amino acids, such as 275 to 300 amino acids, for example 300 to 325 amino acids, such as 325 to 350 amino acids, for example 350 to 375 amino acids, such as 375 to 400 amino acids, for example 400 to 425 amino acids, such as 425 to 450 amino acids, for example 450 to 475 amino acids, such as 475 to 500 amino acids, for example 500 to 525 amino acids, such as 525 to 550 amino acids, for example 550 to 575 amino acids, such as 575 to 600 amino acids, for example 600 to 625 amino acids, such as 625 to 640 amino acids derived from Hsp70.

A fragment of Hsp70 is in one embodiment a truncated version of the wild type protein. A fragment may be truncated by shortening of the protein from either the amino-terminal or the carboxy-terminal ends of the protein, or it may be truncated by deletion of one or more internal regions of any size of the protein.

In one embodiment the Hsp70 is a variant of a fragment, i.e. a fragment of Hsp70 as defined herein wherein one or more amino acids are substituted as defined herein.

It is appreciated that the exact quantitative effect of the functional fragment or variant may be different from the effect of the full-length molecule. In some instances, the functional fragment or variant may indeed be more effective than the full-length molecule.

The present invention also relates to variants of Hsp70, or fragments thereof, wherein the substitutions have been designed by computational analysis that uses sequence homology to predict whether a substitution affects protein function (e.g. Pauline C. Ng and Steven Henikoff, Genome Research, Vol. 11, Issue 5, 863-874, May 2001).

Ectopic Expression of Hsp70

In one embodiment, Hsp70, or a functional fragment or variant thereof, is expressed from a vector. In one embodiment Hsp70, or a functional fragment or variant thereof, is administered to an individual in need thereof in the form of a vector.

The vector used for expressing Hsp70, or a functional fragment or variant thereof, is in one embodiment selected from the group consisting of: viral vectors (retroviral and adenoviral) or non-viral vectors (e.g. plasmid, cosmid, bacteriophage).

In one embodiment, said vector comprises one or more of an origin of replication, a marker for selection and one or more recognition sites for a restriction endonuclease. In another embodiment, said vector is operably linked to regulatory sequences controlling the transcription of said Hsp70, or a functional fragment or variant thereof, in a suitable host cell.

In one embodiment there is provided a method for producing Hsp70, or a functional fragment or variant thereof, as described herein; said method comprising the steps of providing a vector encoding said Hsp70, or a functional fragment or variant thereof, and expressing said vector either in vitro, or in vivo in a suitable host organism, thereby producing said Hsp70, or a functional fragment or variant thereof.

In one embodiment there is provided an isolated recombinant or transgenic host cell comprising a vector encoding Hsp70, or a functional fragment or variant thereof, as defined herein.

In one embodiment there is provided a method for generating a recombinant or transgenic host cell, said method comprising the steps of providing a vector encoding Hsp70, or a functional fragment or variant thereof, introducing said vector into said recombinant or transgenic host cell and optionally also expressing said vector in said recombinant or transgenic host cell, thereby generating a recombinant or transgenic host cell producing said Hsp70, or a functional fragment or variant thereof.

In another embodiment there is provided a transgenic, mammalian organism comprising the host cell producing said Hsp70, or a functional fragment or variant thereof. In a further embodiment, the transgenic, mammalian organism comprising the recombinant or transgenic host cell according to the present invention is non-human. The transgenic host cell can be selected from the group consisting of a mammalian, plant, bacterial, yeast or fungal host cell.

To improve the delivery of the DNA into the cell, the DNA must be protected from damage and its entry into the cell must be facilitated. Lipoplexes and polyplexes, have been created that have the ability to protect the DNA from undesirable degradation during the transfection process. Plasmid DNA can be covered with lipids in an organized structure like a micelle or a liposome. When the organized structure is complexed with DNA it is called a lipoplex. There are three types of lipids that may be employed for forming liposomes; anionic (negatively charged), neutral, or cationic (positively charged). Complexes of polymers with DNA are called polyplexes. Most polyplexes consist of cationic polymers and their production is regulated by ionic interactions.

In one embodiment, the vector comprising Hsp70, or a functional fragment or variant thereof, may be used for gene therapy. Gene therapy is the insertion of genes into an individual's cells and tissues to treat a disease, such as a hereditary disease in which a deleterious mutant allele is replaced with a functional one.

In another embodiment, Hsp70, or a functional fragment or variant thereof, may be administered as naked DNA. This is the simplest form of non-viral transfection. Delivery of naked DNA may be performed by use of electroporation, sonoporation, or the use of a "gene gun", which shoots DNA coated gold particles into a cell using high pressure gas.

Inducers of Heat Shock Proteins, Including Hsp70

In one embodiment the bioactive agent activates the heat shock response. In one embodiment the bioactive agent increases the intracellular concentration and/or activity of one or more heat shock proteins, including Hsp70. In one embodiment the bioactive agent increases the intracellular concentration (or level) and/or activity of Hsp70. In one embodiment the bioactive agent increases the intracellular concentration (or level) of Hsp70. In one embodiment the bioactive agent is an inducer of one or more heat shock proteins, including Hsp70. In one embodiment the bioactive agent is an inducer of Hsp70.

It is an aspect of the present invention to provide an inducer of one or more heat shock proteins, including Hsp70, for use in treating a disease associated with dysregulation of cholesterol homeostasis.

It is an aspect of the present invention to provide an inducer of Hsp70 for use in treating a disease associated with dysregulation of cholesterol homeostasis.

In one embodiment there is provided use of an inducer of one or more heat shock proteins, including Hsp70, for the manufacture of a medicament for the treatment of a disease associated with dysregulation of cholesterol homeostasis.

In one embodiment there is provided a method of treating a disease associated with dysregulation of cholesterol homeostasis, said method comprising one or more steps of administering an inducer of one or more heat shock proteins, including Hsp70, to an individual in need thereof.

Small Molecule Inducers of Heat Shock Proteins

In one embodiment the bioactive agent is an inducer of Hsp70. In one embodiment the inducer of Hsp70 is a small molecule inducer of heat shock proteins, including Hsp70. In one embodiment the inducer of Hsp70 is a small molecule inducer of Hsp70.

In one embodiment an inducer of Hsp70; or a small molecule inducer of one or more heat shock proteins, including Hsp70; is a compound capable of increasing the intracellular concentration (or level) of inter alia Hsp70, such as by amplifying Hsp70 gene expression. An inducer of Hsp70 may also induce other heat shock proteins.

In one embodiment the bioactive agent is capable of increasing the intracellular concentration (or level) of Hsp70 by amplifying Hsp70 gene expression. In one embodiment the bioactive agent is capable of increasing the intracellular concentration (or level) of Hsp70 by amplifying Hsp70 gene expression, wherein said bioactive agent is a hydroxylamine derivative, such as a hydroxylamine derivative small molecule.

Examples of such hydroxylamine derivatives include arimoclomol, iroxanadine, bimoclomol, BGP-15, their stereoisomers and the acid addition salts thereof.

It is an aspect of the present invention to provide a small molecule inducer of Hsp70 for use in treating a disease associated with dysregulation of cholesterol homeostasis.

In one embodiment there is provided use of a small molecule inducer of Hsp70 for the manufacture of a medicament for the treatment of a disease associated with dysregulation of cholesterol homeostasis.

In one embodiment there is provided a method of treating a disease associated with dysregulation of cholesterol homeostasis, said method comprising one or more steps of administering a small molecule inducer of Hsp70 to an individual in need thereof.

Arimoclomol

In one embodiment the small molecule inducer of Hsp70 is selected from N-[2-hydroxy-3-(1-piperidinyl)-propoxy]-pyridine-1-oxide-3-carboximidoyl chloride (arimoclomol), its stereoisomers and the acid addition salts thereof. Arimoclomol is further described in e.g. WO 00/50403.

In one embodiment the small molecule inducer of Hsp70 is selected from N-[2-hydroxy-3-(1-piperidinyl)-propoxy]-pyridine-1-oxide-3-carboximidoyl chloride (arimoclomol), its optically active (+) or (−) enantiomer, a mixture of the enantiomers of any ratio, and the racemic compound, furthermore, the acid addition salts formed from any of the above compounds with mineral or organic acids constitute objects of the present invention. All possible geometrical isomer forms of N-[2-hydroxy-3-(1-piperidinyl)-propoxy]-pyridine-1-oxide-3-carboximidoyl chloride belong to the scope of the invention. The term "the stereoisomers of N-[2-hydroxy-3-(1-piperidinyl)-propoxy]-pyridine-1-oxide-3-carboximidoyl chloride" refers to all possible optical and geometrical isomers of the compound.

If desired, the N-[2-hydroxy-3-(1-piperidinyl)-propoxy]-pyridine-1-oxide-3-carboximidoyl chloride or one of its optically active enantiomers can be transformed into an acid addition salt with a mineral or organic acid, by known methods.

In one embodiment the small molecule inducer of Hsp70 is the racemate of N-[2-hydroxy-3-(1-piperidinyl)-propoxy]-pyridine-1-oxide-3-carboximidoyl chloride.

In one embodiment the small molecule inducer of Hsp70 is an optically active stereoisomer of N-[2-hydroxy-3-(1-piperidinyl)-propoxy]-pyridine-1-oxide-3-carboximidoyl chloride.

In one embodiment the small molecule inducer of Hsp70 is an enantiomer of N-[2-hydroxy-3-(1-piperidinyl)-propoxy]-pyridine-1-oxide-3-carboximidoyl chloride.

In one embodiment the small molecule inducer of Hsp70 is selected from the group consisting of (+)—R—N-[2-hydroxy-3-(1-piperidinyl)-propoxy]-pyridine-1-oxide-3-carboximidoyl chloride and (−)—(S)—N-[2-hydroxy-3-(1-piperidinyl)-propoxy]-pyridine-1-oxide-3-carboximidoyl chloride.

In one embodiment the small molecule inducer of Hsp70 is an acid addition salt of N-[2-hydroxy-3-(1-piperidinyl)-propoxy]-pyridine-1-oxide-3-carboximidoyl chloride.

In one embodiment the small molecule inducer of Hsp70 is selected from the group consisting of N-[2-hydroxy-3-(1-piperidinyl)-propoxy]-pyridine-1-oxide-3-carboximidoyl chloride citrate (BRX-345), and N-[2-hydroxy-3-(1-piperidinyl)-propoxy]-pyridine-1-oxide-3-carboximidoyl chloride maleate (BRX-220).

In one embodiment the small molecule inducer of Hsp70 is selected from the group consisting of (+)—R—N-[2-hydroxy-3-(1-piperidinyl)-propoxy]-pyridine-1-oxide-3-carboximidoyl chloride citrate; (−)—S—N-[2-hydroxy-3-(1-piperidinyl)-propoxy]-pyridine-1-oxide-3-carboximidoyl chloride citrate; (+)—R—N-[2-hydroxy-3-(1-piperidinyl)-propoxy]-pyridine-1-oxide-3-carboximidoyl chloride maleate; and (−)—S—N-[2-hydroxy-3-(1-piperidinyl)-propoxy]-pyridine-1-oxide-3-carboximidoyl chloride maleate.

BGP-15

In one embodiment the small molecule inducer of Hsp70 is N-[2-hydroxy-3-(1-piperidinyl)propoxy]-3-pyridinecarboximidamide, dihydrochloride (BGP-15), its stereoisomers and the acid addition salts thereof.

In one embodiment the small molecule inducer of Hsp70 is selected from N-[2-hydroxy-3-(1-piperidinyl)propoxy]-3-pyridinecarboximidamide, dihydrochloride (BGP-15), its optically active (+) or (−) enantiomer, a mixture of the enantiomers of any ratio, and the racemic compound, furthermore, the acid addition salts formed from any of the above compounds with mineral or organic acids constitute objects of the present invention. All possible geometrical isomer forms of N-[2-hydroxy-3-(1-piperidinyl)propoxy]-3-pyridinecarboximidamide, dihydrochloride belong to the scope of the invention. The term "the stereoisomers of N-[2-hydroxy-3-(1-piperidinyl)propoxy]-3-pyridinecarboximidamide, dihydrochloride" refers to all possible optical and geometrical isomers of the compound.

Iroxanadine

In one embodiment the small molecule inducer of Hsp70 is selected from 5,6-dihydro-5-(1-piperidinyl)methyl-3-(3-pyridyl)-4H-1,2,4-oxadiazine (iroxanadine), its stereoisomers and the acid addition salts thereof. Iroxanadine is further described in e.g. WO 97/16439 and WO 00/35914.

In one embodiment the small molecule inducer of Hsp70 is selected from 5,6-dihydro-5-(1-piperidinyl)methyl-3-(3-pyridyl)-4H-1,2,4-oxadiazine (iroxanadine), its optically active (+) or (−) enantiomer, a mixture of the enantiomers of any ratio, and the racemic compound, furthermore, the acid addition salts formed from any of the above compounds with mineral or organic acids constitute objects of the present invention. All possible geometrical isomer forms of 5,6-dihydro-5-(1-piperidinyl)methyl-3-(3-pyridyl)-4H-1,2,4-oxadiazine belong to the scope of the invention. The term "the stereoisomers of 5,6-dihydro-5-(1-piperidinyl)methyl-3-(3-pyridyl)-4H-1,2,4-oxadiazine" refers to all possible optical and geometrical isomers of the compound.

If desired, the 5,6-dihydro-5-(1-piperidinyl)methyl-3-(3-pyridyl)-4H-1,2,4-oxadiazine or one of its optically active enantiomers can be transformed into an acid addition salt with a mineral or organic acid, by known methods.

In one embodiment the small molecule inducer of Hsp70 is the racemate of 5,6-dihydro-5-(1-piperidinyl)methyl-3-(3-pyridyl)-4H-1,2,4-oxadiazine.

In one embodiment the small molecule inducer of Hsp70 is an optically active stereoisomer of 5,6-dihydro-5-(1-piperidinyl)methyl-3-(3-pyridyl)-4H-1,2,4-oxadiazine.

In one embodiment the small molecule inducer of Hsp70 is an enantiomer of 5,6-dihydro-5-(1-piperidinyl)methyl-3-(3-pyridyl)-4H-1,2,4-oxadiazine.

In one embodiment the small molecule inducer of Hsp70 is selected from the group consisting of (+)-5,6-dihydro-5-(1-piperidinyl)methyl-3-(3-pyridyl)-4H-1,2,4-oxadiazine and (−)-5,6-dihydro-5-(1-piperidinyl)methyl-3-(3-pyridyl)-4H-1,2,4-oxadiazine.

In one embodiment the small molecule inducer of Hsp70 is an acid addition salt of 5,6-dihydro-5-(1-piperidinyl)methyl-3-(3-pyridyl)-4H-1,2,4-oxadiazine.

In one embodiment the small molecule inducer of Hsp70 is selected from the group consisting of 5,6-dihydro-5-(1-piperidinyl)methyl-3-(3-pyridyl)-4H-1,2,4-oxadiazine citrate, and 5,6-dihydro-5-(1-piperidinyl)methyl-3-(3-pyridyl)-4H-1,2,4-oxadiazine maleate.

In one embodiment the small molecule inducer of Hsp70 is selected from the group consisting of (+)-5,6-dihydro-5-(1-piperidinyl)methyl-3-(3-pyridyl)-4H-1,2,4-oxadiazine citrate; (+5,6-dihydro-5-(1-piperidinyl)methyl-3-(3-pyridyl)-4H-1,2,4-oxadiazine citrate; (+)-5,6-dihydro-5-(1-piperidinyl)methyl-3-(3-pyridyl)-4H-1,2,4-oxadiazine maleate; and (−)-5,6-dihydro-5-(1-piperidinyl)methyl-3-(3-pyridyl)-4H-1,2,4-oxadiazine maleate.

Bimoclomol

In one embodiment the small molecule inducer of Hsp70 is selected from N-[2-hydroxy-3-(1-piperidinyl)-propoxy]-3-pyridinecarboximidoyl chloride (bimoclomol) its stereoisomers and the acid addition salts thereof. Bimoclomol is further described in e.g. WO 1997/16439.

In one embodiment the small molecule inducer of Hsp70 is selected from N-[2-hydroxy-3-(1-piperidinyl)-propoxy]-3-pyridinecarboximidoyl chloride (bimoclomol), its optically active (+) or (−) enantiomer, a mixture of the enantiomers of any ratio, and the racemic compound, furthermore, the acid addition salts formed from any of the above compounds with mineral or organic acids constitute objects of the present invention. All possible geometrical isomer forms of N-[2-hydroxy-3-(1-piperidinyl)-propoxy]-3-pyridinecarboximidoyl chloride belong to the scope of the invention. The term "the stereoisomers of N-[2-hydroxy-3-(1-piperidinyl)-propoxy]-3-pyridinecarboximidoyl chloride" refers to all possible optical and geometrical isomers of the compound.

If desired, the N-[2-hydroxy-3-(1-piperidinyl)-propoxy]-3-pyridinecarboximidoyl chloride or one of its optically active enantiomers can be transformed into an acid addition salt with a mineral or organic acid, by known methods.

In one embodiment the small molecule inducer of Hsp70 is the racemate of N-[2-hydroxy-3-(1-piperidinyl)-propoxy]-3-pyridinecarboximidoyl chloride.

In one embodiment the small molecule inducer of Hsp70 is an optically active stereoisomer of N-[2-hydroxy-3-(1-piperidinyl)-propoxy]-3-pyridinecarboximidoyl chloride.

In one embodiment the small molecule inducer of Hsp70 is an enantiomer of N-[2-hydroxy-3-(1-piperidinyl)-propoxy]-3-pyridinecarboximidoyl chloride.

In one embodiment the small molecule inducer of Hsp70 is selected from the group consisting of (+)—R—N-[2-hydroxy-3-(1-piperidinyl)-propoxy]-3-pyridinecarboximidoyl chloride and (−)—S—N-[2-hydroxy-3-(1-piperidinyl)-propoxy]-3-pyridinecarboximidoyl chloride.

In one embodiment the small molecule inducer of Hsp70 is an acid addition salt of N-[2-hydroxy-3-(1-piperidinyl)-propoxy]-3-pyridinecarboximidoyl chloride.

In one embodiment the small molecule inducer of Hsp70 is selected from the group consisting of N-[2-hydroxy-3-(1-piperidinyl)-propoxy]-3-pyridinecarboximidoyl chloride citrate, and N-[2-hydroxy-3-(1-piperidinyl)-propoxy]-3-pyridinecarboximidoyl chloride maleate.

In one embodiment the small molecule inducer of Hsp70 is selected from the group consisting of (+)—R—N-[2-hydroxy-3-(1-piperidinyl)-propoxy]-3-pyridinecarboximidoyl chloride citrate; (−)—S—N-[2-hydroxy-3-(1-piperidinyl)-propoxy]-3-pyridinecarboximidoyl chloride citrate; (+)—R—N-[2-hydroxy-3-(1-piperidinyl)-propoxy]-3-pyridinecarboximidoyl chloride maleate; and (−)—S—N-[2-hydroxy-3-(1-piperidinyl)-propoxy]-3-pyridinecarboximidoyl chloride maleate.

Inducers for Treatment

In one embodiment there is provided a bioactive agent capable of increasing the intracellular concentration of Hsp70 by amplifying Hsp70 gene expression, wherein said bioactive agent is a hydroxylamine derivative,
wherein said bioactive agent is selected from the group consisting of:
N-[2-hydroxy-3-(1-piperidinyl)-propoxy]-pyridine-1-oxide-3-carboximidoyl chloride (arimoclomol), its stereoisomers and the acid addition salts thereof,
5,6-dihydro-5-(1-piperidinyl)methyl-3-(3-pyridyl)-4H-1,2,4-oxadiazine (iroxanadine), its stereoisomers and the acid addition salts thereof,
N-[2-hydroxy-3-(1-piperidinyl)-propoxy]-3-pyridinecarboximidoyl chloride (bimoclomol) its stereoisomers and the acid addition salts thereof, and
N-[2-hydroxy-3-(1-piperidinyl)propoxy]-3-pyridinecarboximidamide, dihydrochloride (BGP-15), its stereoisomers and the acid addition salts thereof,
for use in the treatment of a disease associated with dysregulation of cholesterol homeostasis.

In one embodiment there is provided a bioactive agent capable of increasing the intracellular concentration of Hsp70 by amplifying Hsp70 gene expression, wherein said bioactive agent is a hydroxylamine derivative,
wherein said bioactive agent is selected from the group consisting of:
N-[2-hydroxy-3-(1-piperidinyl)-propoxy]-pyridine-1-oxide-3-carboximidoyl chloride (arimoclomol), its stereoisomers and the acid addition salts thereof,
5,6-dihydro-5-(1-piperidinyl)methyl-3-(3-pyridyl)-4H-1,2,4-oxadiazine (iroxanadine), its stereoisomers and the acid addition salts thereof,
N-[2-hydroxy-3-(1-piperidinyl)-propoxy]-3-pyridinecarboximidoyl chloride (bimoclomol) its stereoisomers and the acid addition salts thereof, and
N-[2-hydroxy-3-(1-piperidinyl)propoxy]-3-pyridinecarboximidamide, dihydrochloride (BGP-15), its stereoisomers and the acid addition salts thereof,
for use in the treatment of a disease associated with dysregulation of cholesterol homeostasis selected from the group consisting of Smith-Lemli-Opitz Syndrome (SLOS), Antley-Bixler Syndrome, Hydrops-Ectopic Calcification-Moth-Eaten Skeletal Dysplasia (Greenberg dysplasia), Congenital Hemidysplasia with Ichthyosiform Nevus and Limb Defects Syndrome (CHILD), CK Syndrome, Conradi-Hünermann-Happle Syndrome (CPDX2, X-linked dominant chondrodysplasia punctate type 2), Lathosterolosis, Desmosterolosis, Mevalonate Kinase Deficiency (MKD) or (HIDS), Mevalonate Aciduria, atherosclerosis, Tangier disease and familial HDL deficiency.

In one embodiment there is provided a compound selected from the group consisting of (+)—R—N-[2-hydroxy-3-(1-piperidinyl)-propoxy]-pyridine-1-oxide-3-carboximidoyl chloride citrate; (−)—S—N-[2-hydroxy-3-(1-piperidinyl)-propoxy]-pyridine-1-oxide-3-carboximidoyl chloride citrate; (+)—R—N-[2-hydroxy-3-(1-piperidinyl)-propoxy]-pyridine-1-oxide-3-carboximidoyl chloride maleate; and (−)—S—N-[2-hydroxy-3-(1-piperidinyl)-propoxy]-pyridine-1-oxide-3-carboximidoyl chloride maleate, for use in the treatment of a disease associated with dysregulation of cholesterol homeostasis, such as Smith-Lemli-Opitz Syndrome (SLOS), Antley-Bixler Syndrome, Hydrops-Ectopic Calcification-Moth-Eaten Skeletal Dysplasia (Greenberg dysplasia), Congenital Hemidysplasia with Ichthyosiform Nevus and Limb Defects Syndrome (CHILD), CK Syndrome, Conradi-Hünermann-Happle Syndrome (CPDX2, X-linked dominant chondrodysplasia punctate type 2), Lathosterolosis, Desmosterolosis, Mevalonate Kinase Deficiency (MKD) or (HIDS), Mevalonate Aciduria, atherosclerosis, Tangier disease and familial HDL deficiency.

Other Inducers of Heat Shock Proteins

In one embodiment the bioactive agent is an inducer of Hsp70. Any means for inducing Hsp70 expression is envisioned to be encompassed herewith, some of which are outlined herein below.

In one embodiment the inducer of Hsp70 is sub-lethal heat therapy. Increasing the temperature of an individual is a potent inducer of HSPs including Hsp70, and as such sub-lethal heat therapy is a means for inducing Hsp70. In one embodiment, sub-lethal heat therapy comprises increasing the temperature of an individual to a core temperature of about 38° C., such as about 39° C., for example about 40° C., such as about 41° C., for example about 42° C., such as about 43° C.

Psychological stress such as predatory fear and electric shock can evoke a stress induced eHsp70 release, a process which is suggested to be dependent on cathecholamine signaling. Further, adrenaline and noradrenalin can evoke Hsp70 release.

A number of compounds have been shown to induce (or co-induce) HSPs, including Hsp70. In one embodiment the inducer of Hsp70 is selected from the group consisting of: membrane-interactive compounds such as alkyllysophospholipid edelfosine (ET-18-OCH3 or 1-octadecyl-2-methyl-rac-glycero-3-phosphocholine); anti-inflammatory drugs including cyclooxygenase ½ inhibitors such as celecoxib and rofecoxib, as well as NSAIDs such as acetyl-salicylic acid, sodium salicylate and indomethacin; dexamethasone; prostaglandins PGA1, PGj2 and 2-cyclopentene-1-one; peroxidase proliferator-activated receptor-gamma agonists; tubulin-interacting anticancer agents including vincristine and paclitaxel; the insulin sensitizer pioglitazone; anti-neoplastic agents such as carboplatin, doxorubicin, fludarabine, ifosfamide and cytarabine; Hsp90 inhibitors including geldanamycin, 17-AAG, 17-DMAG, radicicol, herbimycin-A and arachidonic acid; proteasome inhibitors such as MG132, lactacystin, Bortezomib, Carfilzomib and Oprozomib; serine protease inhibitors such as DCIC, TLCK and TPCK; Histone Deacetylase Inhibitors (HDACi) including SAHA/vorinostat, Belinostat/PXD101, LB-205, LBH589 (panobinostat), FK-228, CI-994, trichostatin A (TSA) and PCI-34051; anti-ulcer drugs including geranylgeranylacetone (GGA), rebamipide, carbenoxolone and polaprezinc (zinc L-carnosine); heavy metals (zinc and tin); cocaine; nicotine; alcohol; alpha-adrenergic agonists; cyclopentenone prostanoids; L-type Ca++ channel blockers, such as L-type Ca++channel blockers that also inhibits ryanodine receptors, such as lacidipine; ryanodine receptor antagonists such as DHBP (1,1'-diheptyl-4,4'-bipyridium; as well as herbal medicines including paeoniflorin, glycyrrhizin, celastrol, dihydrocelastrol, dihydrocelastrol diacetate and curcumin.

In one embodiment the inducer of Hsp70 is a proteasome inhibitor. In one embodiment the proteasome inhibitor is selected from the group consisting of Bortezomib, Carfilzomib, Oprozomib, MG132 and lactacystin.

In one embodiment the inducer of Hsp70 is a HDAC inhibitor. In one embodiment the HDACi is selected form the group consisting of SAHA/vorinostat, Belinostat/PXD101, LB-205, LBH589 (panobinostat), FK-228, CI-994, trichostatin A (TSA) and PCI-34051.

Membrane Fluidizers In one embodiment the inducer of Hsp70 is is a membrane fluidizer. Treatment with a membrane fluidizer may also be termed lipid therapy.

Besides the denaturation of a proportion of cellular proteins during heat (proteotoxicity), a change in the fluidity of membranes is also proposed as being a cellular thermosensor that initiates the heat shock response and induces HSPs. Indeed, chemically induced membrane perturbations—analogous with heat induced plasma membrane fluidization—are capable of activating HSP, without causing protein denaturation.

In one embodiment the inducer of Hsp70 is a membrane fluidizer selected from the group consisting of benzyl alcohol, heptanol, AL721, docosahexaenoic acid, aliphatic alcohols, oleyl alcohol, dimethylaminoethanol, $A_2C$, farnesol and anaesthetics such as lidocaine, ropivacaine, bupivacaine and mepivacaine, as well as others known to the skilled person.

Diseases Associated with Dysregulation of Cholesterol Homeostasis

Provided herewith are bioactive agents as defined herein that increase the intracellular concentration (or level 9 and/or activity of one or more heat shock proteins, including Hsp70, for treating a disease associated with dysregulation of cholesterol homeostasis.

In one embodiment a disease associated with dysregulation of cholesterol homeostasis is a disease associated with cholesterol accumulation (or cholesterol storage), such as intracellular cholesterol accumulation.

In one embodiment a disease associated with dysregulation of cholesterol homeostasis is a disease associated with abnormal cholesterol accumulation (or cholesterol storage), such as abnormal intracellular cholesterol accumulation.

In one embodiment a disease associated with dysregulation of cholesterol homeostasis is a disease (or disorder) of cholesterol metabolism. In one embodiment the disease of cholesterol metabolism is an inborn error of cholesterol metabolism.

In one embodiment the disease of cholesterol metabolism is a disease of cholesterol biosynthesis. In one embodiment the disease of cholesterol biosynthesis is an inborn disease of cholesterol biosynthesis.

In one embodiment the disease of cholesterol biosynthesis is selected from the group consisting of:
Smith-Lemli-Opitz Syndrome (SLOS),
Antley-Bixler Syndrome,
Hydrops-Ectopic Calcification-Moth-Eaten Skeletal Dysplasia (Greenberg dysplasia),
Congenital Hemidysplasia with Ichthyosiform Nevus and Limb Defects Syndrome (CHILD),
CK Syndrome,
Conradi-Hünermann-Happle Syndrome (CPDX2, X-linked dominant chondrodysplasia punctate type 2),
Lathosterolosis,
Desmosterolosis,
Mevalonate Kinase Deficiency (MKD) also known as Hyper IgD Syndrome (HIDS), and
Mevalonate Aciduria or mevalonic aciduria (MVA).

In one embodiment the disease of cholesterol metabolism is a disease of cholesterol trafficking.

In one embodiment the disease of cholesterol metabolism is a disease of cholesterol transport.

In one embodiment the disease of cholesterol metabolism is a disease associated with cholesterol efflux.

In one embodiment the disease as defined associated with dysregulation of cholesterol homeostasis as defined herewith is not selected from the group consisting of cerebrotendinous cholesterosis, Wolman's disease and cholesteryl ester storage disease. In one embodiment the disease as defined associated with dysregulation of cholesterol homeostasis as defined herewith is not a lysosomal cholesterol storage disease.

In one embodiment the disease of cholesterol metabolism is a disease associated with the cholesterol transporter ABCA1. In one embodiment the disease of cholesterol metabolism is an ABCA1-related disease. In one embodiment the ABCA1-related disease is selected from the group consisting of ABCA1-deficiencies, ABCA1-mutations and diseases associated with impaired ABCA1-regulation.

In one embodiment the disease of cholesterol transport, or cholesterol efflux, is familial HDL deficiency. In one embodiment the disease associated with ABCA1 is familial HDL deficiency. Familial HDL deficiency is caused by a mutation in the ABCA1-gene. It is a condition characterized by low levels of high-density lipoprotein (HDL) in the blood. Familial HDL deficiency is inherited in an autosomal dominant pattern, which means an alteration in one copy of either the ABCA1 or the APOA1 gene in each cell is sufficient to cause the disorder. People with alterations in both copies of the ABCA1 gene develop the related disorder Tangier disease.

In one embodiment the disease of cholesterol transport, or cholesterol efflux, is Tangier disease. In one embodiment the disease associated with ABCA1 is Tangier disease. Tangier disease is caused by a mutation in the ABCA1-gene. Patients have little or no circulating HDL and accumulate cholesterol, leading to the formation of foam cells (an early marker of atherosclerosis).

To date there is no specific treatment for Tangier disease. Drugs known to increase HDL levels have been shown to be ineffective in Tangier patients.

Provided herewith are bioactive agents that increase the intracellular concentration and/or activity of Hsp70, including Hsp70 protein and Hsp70 inducers, for treating a disease associated with dysregulation of cholesterol homeostasis, including diseases associated with cholesterol accumulation, diseases of cholesterol metabolism, diseases of cholesterol biosynthesis, diseases of cholesterol trafficking and diseases of cholesterol transport or efflux.

Provided herewith are bioactive agents that increase the intracellular concentration and/or activity of Hsp70, including Hsp70 protein and Hsp70 inducers, for treating a disease selected from the group consisting of Smith-Lemli-Opitz Syndrome (SLOS), Antley-Bixler Syndrome, Hydrops-Ectopic Calcification-Moth-Eaten Skeletal Dysplasia (Greenberg dysplasia), Congenital Hemidysplasia with Ichthyosiform Nevus and Limb Defects Syndrome (CHILD), CK Syndrome, Conradi-Hünermann-Happle Syndrome (CPDX2, X-linked dominant chondrodysplasia punctate type 2), Lathosterolosis, Desmosterolosis, Mevalonate Kinase Deficiency (MKD) or (HIDS), Mevalonate Aciduria and Tangier disease.

Also provided are bioactive agents that increase the intracellular concentration and/or activity of Hsp70, including Hsp70 protein and Hsp70 inducers, for treating a disease associated with foam cells. In one embodiment a disease associated with foam cells comprise atherosclerosis and Tangier disease.

Atherosclerosis

In one embodiment the disease associated with cholesterol accumulation is atherosclerosis (also known as arteriosclerotic vascular disease).

It is thus an aspect to provide a bioactive agent as defined herein that increase the intracellular concentration and/or activity of one or more heat shock proteins, including Hsp70, for treating atherosclerosis.

Also encompassed are bioactive agents as defined herein for use in methods of reducing (inhibiting, reversing) atheromatous plaques and/or fatty streaks.

Atherosclerosis is a specific form of arteriosclerosis in which an artery-wall thickens as a result of invasion and accumulation of white blood cells (WBCs) and proliferation of intimal-smooth-muscle cell creating a fibro fatty plaque (atheromatous plaque). The accumulation of the white blood cells is termed "fatty streaks" early on, and contains both living, active WBCs (producing inflammation) and remnants of dead cells, including cholesterol and triglycerides. The plaque is divided into the atheroma, underlying areas of cholesterol crystals and calcification at the outer base of older or more advanced lesions.

Atherosclerosis is initiated by inflammatory processes in the endothelial cells of the vessel wall associated with retained low-density lipoprotein (LDL) particles. This retention may be a cause, an effect, or both, of the underlying inflammatory process. Once inside the vessel wall, LDL particles can become more prone to oxidation. Endothelial cells respond by attracting monocyte white blood cells, causing them to leave the blood stream, penetrate into the arterial walls and transform into macrophages. The macrophages' ingestion of oxidized LDL particles triggers a cascade of immune responses which over time can produce an atheroma if HDL removal of fats from the macrophages does not keep up. The immune system's specialized white blood cells (macrophages and T-lymphocytes) absorb the oxidized LDL, forming specialized foam cells. If these foam cells are not able to process the oxidized LDL and recruit HDL particles to remove the fats, they grow and eventually rupture, leaving behind cellular membrane remnants, oxidized materials, and fats (including cholesterol) in the artery wall. This attracts more white blood cells, resulting in a snowballing progression that continues the cycle, inflaming the artery.

ABCA1 mediates the efflux of cholesterol and phospholipids to lipid-poor apolipo-proteins (apo-A1 and apoE), which then form nascent high-density lipoproteins (HDL). Downregulation of ABCA1 in senescent macrophages disrupts the cell's ability to remove cholesterol from its cytoplasm, leading the cells to promote atherogenesis.

Atherosclerosis is a chronic disease that may be asymptotic for years. Atherosclerosis increases the risk of thrombus formation in the lumen or complete closure of the lumen (stenosis) of vessels, of thromboembolism, and resulting ischemia or infarction. Accompanying incidents include myocardial infarction (a heart attack due to thrombosis of a coronary artery), stroke (thrombosis of cerebral and/or carotid arteries), claudication from insufficient blood supply to the legs, and thrombosis of renal and femoral arteries.

Also encompassed are bioactive agents as defined herein for use in methods of reducing (inhibiting, reversing) the risk of thrombus formation, thromboembolism, and resulting ischemia or infarction in individuals with atherosclerosis.

Methods

In one embodiment there is provided a method of stimulating cholesterol efflux from macrophages, such as lipid-laden macrophages, such as foam cells, said method comprising one or more steps of administering a bioactive agent that increase the intracellular concentration and/or activity of Hsp70, including Hsp70 protein and Hsp70 inducers.

In another embodiment there is provided a method of stimulating the decrease of cholesterol esters in macrophages, such as lipid laden macrophages, such as foam cells, said method comprising one or more steps of administering a bioactive agent that increase the intracellular concentration and/or activity of Hsp70, including Hsp70 protein and Hsp70 inducers.

In one embodiment there is provided a method of facilitating cholesterol reduction during macrophage foam cell reversal, and/or reducing intracellular cholesterol in macrophages, such as lipid laden macrophages, such as foam cells, said method comprising one or more steps of administering a bioactive agent that increase the intracellular concentration and/or activity of Hsp70, including Hsp70 protein and Hsp70 inducers.

Also provided is a method of increasing or stimulating ABCA1 levels and/or activity, said method comprising one or more steps of administering a bioactive agent that increase the intracellular concentration and/or activity of Hsp70, including Hsp70 protein and Hsp70 inducers.

In one embodiment stimulating ABCA1 level and/or activity comprise increasing ABCA1-protein levels and/or activity. In one embodiment stimulating ABCA1 level and/or activity comprise increasing ABCA1-mRNA levels and/or activity.

In one embodiment said methods are in vivo. In another embodiment said methods are in vitro or ex vivo.

Composition

Whilst it is possible for the bioactive agents to be administered as the raw chemical, it is in some embodiments preferred to present them in the form of a pharmaceutical formulation. Accordingly, also provided herewith is a composition, such as a pharmaceutical composition, i.e. a pharmaceutically safe composition, comprising a bioactive agent as defined herein. The composition in one embodiment comprises a pharmaceutically and/or physiologically acceptable carriers or excipients.

Pharmaceutical compositions containing a bioactive agent of the present invention may be prepared by conventional techniques, e.g. as described in Remington: The Science and Practice of Pharmacy, 20$^{th}$ Edition, Gennaro, Ed., Mack Publishing Co., Easton, Pa., 2000.

It is thus an aspect to provide a composition, such as a pharmaceutical composition, comprising a bioactive agent that increases the intracellular concentration and/or activity of one or more heat shock proteins, including Hsp70, for use in the treatment of a disease associated with dysregulation of cholesterol homeostasis.

Administration and Dosage

A bioactive agent or composition comprising the same as defined herein is in one embodiment administered to individuals in need thereof in pharmaceutically effective doses or a therapeutically effective amount.

A therapeutically effective amount of a bioactive agent is in one embodiment an amount sufficient to cure, prevent, reduce the risk of, alleviate or partially arrest the clinical manifestations of a given disease or disorder and its complications. The amount that is effective for a particular therapeutic purpose will depend on the severity and the sort of the disorder as well as on the weight and general state of the subject. An amount adequate to accomplish this is defined as a "therapeutically effective amount".

In one embodiment, the composition is administered in doses of 1 µg/day to 100 mg/day; such as 1 µg/day to 10 µg/day, such as 10 µg/day to 100 µg/day, such as 100 µg/day to 250 µg/day, such as 250 µg/day to 500 µg/day, such as 500 µg/day to 750 µg/day, such as 750 µg/day to 1 mg/day, such as 1 mg/day to 2 mg/day, such as 2 mg/day to 5 mg/day, or such as 5 mg/day to 10 mg/day, such as 10 mg/day to 20 mg/day, such as 20 mg/day to 30 mg/day, such as 30 mg/day to 40 mg/day, such as 40 mg/day to 50 mg/day, such as 50 mg/day to 75 mg/day, such as 75 mg/day to 100 mg/day, such as 100 mg/day to 150 mg/day, such as 150 mg/day to 200 mg/day, or such as 200 mg/day to 250 mg/day, such as 250 mg/day to 300 mg/day, such as 300 mg/day to 400 mg/day, such as 400 mg/day to 500 mg/day, such as 500 mg/day to 600 mg/day, such as 600 mg/day to 700 mg/day, such as 700 mg/day to 800 mg/day, such as 800 mg/day to 900 mg/day, such as 900 mg/day to 1000 mg/day.

In one embodiment, the bioactive agent or composition is administered at a dose of 1 µg/kg body weight to 100 mg/kg body weight; such as 1 to 10 µg/kg body weight, such as 10 to 100 µg/day, such as 100 to 250 µg/kg body weight, such as 250 to 500 µg/kg body weight, such as 500 to 750 µg/kg body weight, such as 750 µg/kg body weight to 1 mg/kg body weight, such as 1 mg/kg body weight to 2 mg/kg body weight, such as 2 to 5 mg/kg body weight, such as 5 to 10 mg/kg body weight, such as 10 to 20 mg/kg body weight, such as 20 to 30 mg/kg body weight, such as 30 to 40 mg/kg body weight, such as 40 to 50 mg/kg body weight, such as 50 to 75 mg/kg body weight, or such as 75 to 100 mg/kg body weight.

In one embodiment, a dose is administered one or several times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day. In one embodiment, a dose is administered less than once a day, such as once every second day or once a week.

Routes of Administration

It will be appreciated that the preferred route of administration will depend on the general condition and age of the subject to be treated, the nature of the condition to be treated, the location of the tissue to be treated in the body and the active ingredient chosen.

Systemic Treatment

In one embodiment, the route of administration allows for introducing the bioactive agent into the blood stream to ultimately target the sites of desired action.

In one embodiment the routes of administration is any suitable route, such as an enteral route (including the oral, rectal, nasal, pulmonary, buccal, sublingual, transdermal, intracisternal and intraperitoneal administration), and/or a parenteral route (including subcutaneous, intramuscular, intrathecal, intravenous and intradermal administration).

Appropriate dosage forms for such administration may be prepared by conventional techniques.

Parenteral Administration

Parenteral administration is any administration route not being the oral/enteral route whereby the bioactive agent avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the bioactive agent or composition is in one embodiment administered topically to cross any mucosal membrane of an animal, e.g. in the nose, vagina, eye, mouth, genital tract, lungs, gastrointestinal tract, or rectum, for example the mucosa of the nose, or mouth, and accordingly, parenteral administration may also include buccal, sublingual, nasal, rectal, vaginal and intraperitoneal administration as well as pulmonal and bronchial administration by inhalation or installation. In some embodiments, the bioactive agent is administered topically to cross the skin.

In one embodiment, the intravenous, subcutaneous and intramuscular forms of parenteral administration are employed.

Local Treatment

In one embodiment, the bioactive agent or composition is used as a local treatment, i.e. is introduced directly to the site(s) of action. Accordingly, the bioactive agent may be applied to the skin or mucosa directly, or the bioactive agent may be injected into the site of action, for example into the diseased tissue or to an end artery leading directly to the diseased tissue.

Combination Treatment

It is also an aspect to provide a bioactive agent that increases the intracellular concentration and/or activity of one or more heat shock proteins, including Hsp70, for use in the treatment of a disease associated with dysregulation of cholesterol homeostasis, in combination with other treatment modalities.

Thus, in one embodiment, the bioactive agent is administered to an individual in need thereof in combination with at least one other treatment modality, such as conventional or known treatment modalities for diseases associated with dysregulation of cholesterol homeostasis.

Administering more than one treatment modality in combination may occur either simultaneously, or sequentially. Simultaneous administration may be two compounds comprised in the same composition or comprised in separate compositions, or may be one composition and one other treatment modality performed essentially at the same time. Sequential administration means that the more than one treatment modalities are administered at different time points, such as administering one treatment modality first, and administering the second treatment modality subsequently. The time frame for administering more than one treatment modality sequentially may be determined by a skilled person in the art for achieving the optimal effect, and may in one embodiment be between 30 minutes to 72 hours.

The treatment modalities in the form of chemical compounds may be administered together or separately, each at its most effective dosage. Administering more than one compound may have a synergistic effect, thus effectively reducing the required dosage of each drug.

It is also an aspect to provide a composition comprising, separately or together, i) a bioactive agent that increases the intracellular concentration and/or activity of one or more heat shock proteins, including Hsp70, and ii) other treatment modalities, for use in the treatment of a disease associated with dysregulation of cholesterol homeostasis, In one embodiment other treatment modalities, or conventional or known treatment modalities for diseases associated with dysregulation of cholesterol homeostasis, are referred to as further active ingredients.

In one embodiment the bioactive agent that increases the intracellular concentration and/or activity of one or more heat shock proteins, including Hsp70, is administered in combination with, and/or formulated as a combination product, with one or more further active ingredients.

In one embodiment the further active ingredient is selected from one or more active ingredients known and/or employed in the treatment of a disease associated with dysregulation of cholesterol homeostasis, such as one or more active ingredients for a disease selected from the group consisting of: Smith-Lemli-Opitz Syndrome (SLOS), Antley-Bixler Syndrome, Hydrops-Ectopic Calcification-Moth-Eaten Skeletal Dysplasia (Greenberg dysplasia), Congenital Hemidysplasia with Ichthyosiform Nevus and Limb Defects Syndrome (CHILD), CK Syndrome, Conradi-Hünermann-Happle Syndrome (CPDX2, X-linked dominant chondrodysplasia punctate type 2), Lathosterolosis, Desmosterolosis, Mevalonate Kinase Deficiency (MKD) or (HIDS), Mevalonate Aciduria, atherosclerosis, Tangier disease and familial HDL deficiency.

In one embodiment the further active ingredient is a cholesteryl ester transfer protein (CETP) inhibitor such as dalcetrapib and anacetrapib. In one embodiment the further active ingredient is reconstituted forms of HDL. In one embodiment the further active ingredient is LDL-lowering drugs. In one embodiment the further active ingredient is a low-fat diet.

---

Sequences

SEQ ID NO: 1: The protein sequence for Homo sapiens heat shock 70 kDa protein 1A (HSPA1A_HUMAN) (NM_005345.5/UniProtKB-P0DMV8):
MAKAAAIGIDLGTTYSCVGVFQHGKVEIIANDQGNRTTPSYVAFTDTERLIGDAAKNQVALNPQNTVFDA
KRLIGRKFGDPVVQSDMKHWPFQVINDGDKPKVQVSYKGETKAFYPEEISSMVLTKMKEIAEAYLGYPVT
NAVITVPAYFNDSQRQATKDAGVIAGLNVLRIINEPTAAAIAYGLDRTGKGERNVLIFDLGGGTFDVSIL
TIDDGIFEVKATAGDTHLGGEDFDNRLVNHFVEEFKRKHKKDISQNKRAVRRLRTACERAKRTLSSSTQA
SLEIDSLFEGIDFYTSITRARFEELCSDLFRSTLEPVEKALRDAKLDKAQIHDLVLVGGSTRIPKVQKLL
QDFFNGRDLNKSINPDEAVAYGAAVQAAILMGDKSENVQDLLLLDVAPLSLGLETAGGVMTALIKRNSTI
PTKQTQIFTTYSDNQPGVLIQVYEGERAMTKDNNLLGRFELSGIPPAPRGVPQIEVTFDIDANGILNVTA
TDKSTGKANKITITNDKGRLSKEEIERMVQEAEKYKAEDEVQRERVSAKNALESYAFNMKSAVEDEGLKG
KISEADKKKVLDKCQEVISWLDANTLAEKDEFEHKRKELEQVCNPIISGLYQGAGGPGPGGFGAQGPKGG
SGSGPTIEEVD SEQ ID NO: 2: The initiator methionine (M at position 1) of SEQ ID NO: 1 is removed to yield a 640-amino acid long sequence (position 2-641):
AKAAAIGIDLGTTYSCVGVFQHGKVEIIANDQGNRTTPSYVAFTDTERLIGDAAKNQVALNPQNTVFDAK
RLIGRKFGDPVVQSDMKHWPFQVINDGDKPKVQVSYKGETKAFYPEEISSMVLTKMKEIAEAYLGYPVTN
AVITVPAYFNDSQRQATKDAGVIAGLNVLRIINEPTAAAIAYGLDRTGKGERNVLIFDLGGGTFDVSILT
IDDGIFEVKATAGDTHLGGEDFDNRLVNHFVEEFKRKHKKDISQNKRAVRRLRTACERAKRTLSSSTQAS
LEIDSLFEGIDFYTSITRARFEELCSDLFRSTLEPVEKALRDAKLDKAQIHDLVLVGGSTRIPKVQKLLQ
DFFNGRDLNKSINPDEAVAYGAAVQAAILMGDKSENVQDLLLLDVAPLSLGLETAGGVMTALIKRNSTIP
TKQTQIFTTYSDNQPGVLIQVYEGERAMTKDNNLLGRFELSGIPPAPRGVPQIEVTFDIDANGILNVTAT
DKSTGKANKITITNDKGRLSKEEIERMVQEAEKYKAEDEVQRERVSAKNALESYAFNMKSAVEDEGLKGK
ISEADKKKVLDKCQEVISWLDANTLAEKDEFEHKRKELEQVCNPIISGLYQGAGGPGPGGFGAQGPKGGS
GSGPTIEEVD SEQ ID NO: 3: The nucleic acid (DNA) sequence for Homo sapiens heat shock 70 kDa protein 1A (HSPA1A) (NM_005345.5):

```
  1 ataaaagccc aggggcaagc ggtccggata acggctagcc tgaggagctg ctgcgacagt
 61 ccactacctt tttcgagagt gactcccgtt gtcccaaggc ttcccagagc gaacctgtgc
121 ggctgcaggc accggcgcgt cgagtttccg gcgtccggaa ggaccgagct cttctcgcgg
181 atccagtgtt ccgtttccag ccccaatct cagacggag ccgacagaga gcagggaacc
241 ggcatggcca aagccgcggc gatcggcatc gacctgggca ccacctactc ctgcgtgggg
301 gtgttccaac acggcaaggt ggagatcatc gccaacgacc agggcaaccg caccaccccc
361 agctacgtgg ccttcacgga caccgagcgg ctcatcgggg atgcggccaa gaaccaggtg
421 gcgctgaacc cgcagaacac cgtgtttgac gcgaagcggc tgattggccg caagttcggc
```

```
 481 gacccggtgg tgcagtcgga catgaagcac tggcctttcc aggtgatcaa cgacggagac
 541 aagcccaagg tgcaggtgag ctacaagggg gagaccaagg cattctaccc cgaggagatc
 601 tcgtccatgg tgctgaccaa gatgaaggag atcgccgagg cgtacctggg ctacccggtg
 661 accaacgcgg tgatcaccgt gccggcctac ttcaacgact cgcagcgcca ggccaccaag
 721 gatgcgggtg tgatcgcggg gctcaacgtg ctgcggatca tcaacgagcc cacggccgcc
 781 gccatcgcct acggcctgga cagaacgggc aaggggagc gcaacgtgct catctttgac
 841 ctgggcgggg gcaccttcga cgtgtccatc ctgacgatcg acgacggcat cttcgaggtg
 901 aaggccacgg ccggggacac ccacctgggt ggggaacag ttgacaacag gctcgtgaac
 961 cacttcgtgg aggagttcaa gagaaaacac aagaaggaca tcagccagaa caagcgagcc
1021 gtgaggcggc tgcgcaccgc ctgcgagagg gccaagagga ccctgtcgtc cagcacccag
1081 gccagcctgg agatcgactc cctgtttgag ggcatcgact tctacgtc atcaccagg
1141 gcgaggttcg aggagctgtg ctccgacctg ttccgaagca cctcgagcc cgtggagaag
1201 gctctgcgcg acgccaagct ggacaaggcc cagattcacg acctggtcct ggtcggggc
1261 tccacccgca tccccaaggt gcagaagctg ctgcaggact tcttcaacgg cgcgacctg
1321 aacaagagca tcaaccccga cgaggctgtg gcctacgggg cggcggtgca ggcggccatc
1381 ctgatggggg acaagtccga gaacgtgcag gacctgctgc tgctggacgt ggctccctg
1441 tcgctggggc tggagacggc cggaggcgtg atgactgccc tgatcaagcg caactccacc
1501 atccccacca gcagacgca gatcttcacc acctactccg acaaccaacc cggggtgctg
1561 atccaggtgt acgagggcga gagggccatg acgaaagaca caatctgtt ggggcgcttc
1621 gagctgagcg gcatccctcc ggcccccagg ggcgtgccc agatcgaggt gacctttcgac
1681 atcgatgcca acggcatcct gaacgtcacg gccacgaaca agagcaccgg caaggccaac
1741 aagatcacca tcaccaacga caagggccgc ctgagcaagg aggagatcga gcgcatggtg
1801 caggaggcgg agaagtacaa agcggaggac gaggtgcagc gcgagagggt gtcagccaag
1861 aacgccctgg agtcctacgc cttcaacatg aagagcgccg tggaggatga ggggctcaag
1921 ggcaagatca gcgaggcgca caagaagaag gtgctgaca agtgtcaaga ggtcatctcg
1981 tggctggacg ccaacacctt ggccgagaag gacgagtttg agcacaagag gaaggagctg
2041 gagcaggtgt gtaacccat catcagcgga ctgtaccagg gtgccggtgg tccccgggcct
2101 gggggcttcg ggctcagg tcccaaggga gggtctggtt caggccccac cattgaggag
2161 gtagattagg ggcctttcca agattgctgt ttttgttttg gagcttcaag actttgcatt
2221 tcctagtatt tctgtttgtc agttctcaat ttcctgtgtt tgcaatgttg aaattttttg
2281 gtgaagtact gaacttgctt tttttccggt ttctacatgc agagatgaat ttatactgcc
2341 atcttacgac tatttcttct tttttaataca cttaactcag gccattttt aagttggtta
2401 cttcaaagta aataaacttt aaaattcaaa aaaaaaaaa aaaaa
```

SEQ ID NO: 4: The protein sequence for Homo sapiens heat shock 70k Da protein 1B (HSPA1B_HUMAN) (NM_005346.4/UniProtKB-P0DMV9):
MAKAAAIGIDLGTTYSCVGVFQHGKVEIIANDQGNRTTPSYVAFTDTERLIGDAAKNQVALNPQNTVFDA
KRLIGRKFGDPVVQSDMKHWPFQVINDGDKPKVQVSYKGETKAFYPEEISSMVLTKMKEIAEAYLGYPVT
NAVITVPAYFNDSQRQATKDAGVIAGLNVLRIINEPTAAAIAYGLDRTGKGERNVLIFDLGGGTFDVSIL
TIDDGIFEVKATAGDTHLGGEDFDNRLVNHFVEEFKRKHKKDISQNKRAVRRLRTACERAKRTLSSSTQA
SLEIDSLFEGIDFYTSITRARFEELCSDLFRSTLEPVEKALRDAKLDKAQIHDLVLVGGSTRIPKVQKLL
QDFFNGRDLNKSINPDEAVAYGAAVQAAILMGDKSENVQDLLLLDVAPLSLGLETAGGVMTALIKRNSTI
PTKQTQIFTTYSDNQPGVLIQVYEGERAMTKDNNLLGRFELSGIPPAPRGVPQIEVTFDIDANGILNVTA
TDKSTGKANKITITNDKGRLSKEEIERMVQEAEKYKAEDEVQRERVSAKNALESYAFNMKSAVEDEGLKG
KISEADKKKVLDKCQEVISWLDANTLAEKDEFEHKRKELEQVCNPIISGLYQGAGGPGPGGFGAQGPKGG
SGSGPTIEEVD SEQ ID NO: 5: The initiator methionine (M at position 1) of SEQ ID NO: 4 is removed to yield a 640-amino acid long sequence (position 2-641):
AKAAAIGIDLGTTYSCVGVFQHGKVEIIANDQGNRTTPSYVAFTDTERLIGDAAKNQVALNPQNTVFDAK
RLIGRKFGDPVVQSDMKHWPFQVINDGDKPKVQVSYKGETKAFYPEEISSMVLTKMKEIAEAYLGYPVTN
AVITVPAYFNDSQRQATKDAGVIAGLNVLRIINEPTAAAIAYGLDRTGKGERNVLIFDLGGGTFDVSILT
IDDGIFEVKATAGDTHLGGEDFDNRLVNHFVEEFKRKHKKDISQNKRAVRRLRTACERAKRTLSSSTQAS
LEIDSLFEGIDFYTSITRARFEELCSDLFRSTLEPVEKALRDAKLDKAQIHDLVLVGGSTRIPKVQKLLQ
DFFNGRDLNKSINPDEAVAYGAAVQAAILMGDKSENVQDLLLLDVAPLSLGLETAGGVMTALIKRNSTIP
TKQTQIFTTYSDNQPGVLIQVYEGERAMTKDNNLLGRFELSGIPPAPRGVPQIEVTFDIDANGILNVTAT
DKSTGKANKITITNDKGRLSKEEIERMVQEAEKYKAEDEVQRERVSAKNALESYAFNMKSAVEDEGLKGK
ISEADKKKVLDKCQEVISWLDANTLAEKDEFEHKRKELEQVCNPIISGLYQGAGGPGPGGFGAQGPKGGS
GSGPTIEEVD SEQ ID NO:6 The nucleic acid (DNA) sequence for Homo sapiens heat shock 70 kDa protein 1B (HSPA1B) (NM_005346.4):

```
   1 ggaaaacggc cagcctgagg agctgctgcg agggtccgct tcgtctttcg agagtgactc
  61 ccgcggtccc aagcgctttcc agagcgaacc tgtgcggctg caggcaccgg cgtgttgagt
 121 ttccggcgtt ccgaaggact gagctcttgt cgcggatccc gtccgccgtt ccagccccc
 181 agtctcagag cggagcccac agagcagggc accggcatgg ccaaagccgc ggcgatcggc
 241 atcgacctgg gcaccaccta tccctgcgtg ggggtgttcc aacacggcaa ggtggagatc
 301 atcgccaacg accagggcaa ccgcaccacc cccagctacg tggccttcac ggacaccgag
 361 cggctcatcg gggatgcggc caagaaccag gtggcgctga cccgcagaa caccgtgttt
 421 gacgcgaagc ggctgatcgg ccgcaagttc ggcgacccgg tggtgcagtc ggacatgaag
 481 cactggcctt tccaggtgat caacgacgga caagccca aggtgcaggt gagctacaag
 541 ggggagacca aggcattcta ccccgacgag atctcgttgt tgacaagag
 601 gagatcgccg aggcgtacct gggctacccg gtgaccaacg cggtgatcac cgtgccggcc
 661 tacttcaacg actcgcagcg ccaggccacc aaggatgcgg gtgtgatcgc ggggctcaac
 721 gtgctgcgga tcatcaacga gcccacggcc gccgccatcg cctacggcct ggacagaacg
 781 ggcaaggggg agcgcaacgt gctcatcttt gacctgggcg ggggcacctt cgacgtgtcc
 841 atcctgacga tcgacgacgg catcttcgag gtgaaggcca cggccgggga cacccacctg
```

-continued

Sequences

```
 901 ggtggggagg actttgacaa caggctggtg aaccacttcg tggaggagtt caagagaaaa
 961 cacaagaagg acatcagcca gaacaagcga gccgtgaggc ggctgcgcac cgcctgcgag
1021 agggccaaga ggaccctgtc gtccagcacc caggccagcc tggagatcga ctccctgttt
1081 gagggcatcg acttctacac gtccatcacc agggcgaggt tcgaggagct gtgctccgac
1141 ctgttccgaa gcaccctgga gcccgtggag aaggctctgc gcgacgccaa gctggacaag
1201 gcccagattc acgacctggt cctggtcggg ggctccaccc gcatcsccaa ggtgcagaag
1261 ctgctgcagg acttcttcaa cgggcgcgac ctgaacaaga gcatcaaccc cgacgaggct
1321 gtggcctacg gggcggcggt gcaggcggcc atcctgatgg gggacaagtc cgagaacgtg
1381 caggacctgc tgctgctgga cgtggctccc ctgtcgctgg ggctggagac ggccggaggc
1441 gtgatgactg ccctgatcaa gcgcaactcc accatcccca ccaagcagac gcagatcttc
1501 accacctact ccgacaacca acccggggtg ctgatccagg tgtacgaggg cgagagggcc
1561 atgacgaaag acaacaatct gttggggcgc ttcgagctga gcggcatccc tccggccccc
1621 aggggcgtgc cccagatcga ggtgaccttc gacatcgatg ccaacggcat cctgaacgtc
1681 acggccacgg acaagagcac cggcaaggcc aacaagatca ccatcaccaa cgacaagggc
1741 cgcctgagca aggaggagat cgagcgcatg gtgcaggagg cggagaagta caaagcggag
1801 gacgaggtgc agcgcgaagg ggtgtcagcc aagaacgccc tggagtccta cgccttcaac
1861 atgaagagcg ccgtggagga tgaggggctc aagggcaaga tcagcgaggc ggacaagaag
1921 aaggttctgg acaagtgtca agaggtcatc tcgtggctgg acgccaacac cttggccgag
1981 aaggacgagt ttgagcacaa gaggaaggag ctggagcagg tgtgtaaccc catcatcagc
2041 ggactgtacc agggtgccgg tggtcccggg cctggcggct tcgggggctca gggtcccaag
2101 ggagggtctg ggtcaggccc taccattgag gaggtggatt aggggcctttt gttctttagt
2161 atgtttgtct ttgaggtgga ctgttgggac tcaaggactt tgctgctgtt ttcctatgtc
2221 atttctgctt cagctctttg ctgcttcact tctttgtaaa gttgtaacct gatggtaatt
2281 agctggcttc attattttg tagtacaacc gatatgttca ttagaattct ttgcatttaa
2341 tgttgatact gtaagggtgt ttcgttccct ttaaatgaat caacactgcc accttctgta
2401 cgagtttgtt tgttttttt ttttttttt tttttgctt ggcgaaaaca ctacaaaggc
2461 tgggaatgta tgttttata atttgtttat ttaaatatga aaataaaat gttaaacttt
2521 aaaaaaaaaa aaaaaaaaa aaaaaaaaa a
```

EXAMPLES rHsp70 Upregulates ABCA1 and Stimulates Cholesterol Removal from Human Macrophage Foam Cells Materials and Methods Cell Culture Human primary white blood cells, isolated from healthy blood donors were acquired form the Finnish Red Cross (permit number 21/2015). Peripheral blood mononuclear cells (PBMCs) were isolated by Ficoll layering (Boyum, A., 1964) with Ficoll-Paque Premium (GE Healthcare). PBMCs were then differentiated to macrophages during 7 days in vitro cultivation in serum-free macrophage medium (Gibco) in the presence of a differentiation factor (GM-CSF, 10 ng/mL, Invitrogen).

Cholesterol Loading and Efflux

To generate foam cells, PBMC derived macrophages were loaded with 50 µg/mL of acetylated LDL (acLDL) for 3 days, as described previously (Blom, T. et al, 2010). Cholesterol efflux was performed in complete medium (RPMI containing 10% FBS) for 12 h in the presence or absence of His-tagged recombinant wildtype or mutant (rHsp70, 20 ug/ml final concentration, if not mentioned) and W90F mutated recombinant Hsp70 (mut rHSP70) supplied by Orphazyme ApS, Denmark.

Transcript and Protein Analyses

Cells were collected in PBS and centrifuged at 2000 rpm for 10 min at 4° C. Cell pellets were lysed in either RNA lysis buffer or in RIPA buffer containing protease inhibitors for transcript or protein analysis.

Protein lysates were cleared by centrifugation at 12000 rpm for 10 min at 4° C. Protein concentration was determined using the Bio-Rad protein assay kit. Equal amount of total protein was loaded on 8% SDS-polyacrylamide gel and Western blotting was performed using polyclonal anti-ABCA1 antibody (1:500, Novus Biologicals). The primary antibody was detected with anti-rabbit secondary antibody (1:2000, Sigma). The blots were developed using the Enhanced Chemiluminiscense kit (Amersham). Protein bands were normalized to Proact membrane stain (Amresco). Quantitation of protein bands was performed using ImageJ program.

Total RNA was isolated using NucleoSpin RNA isolation kit (Macherey-Nagel). 1.5 µg of total RNA was transcribed using SuperScript VILO cDNA synthesis kit (Invitrogen). abca1 primers Fwd 5'-ACATCCTGAAGCCAATCCTGA, Rev 5'-CTCCTGTCGCATGTCACTCC (Sigma) and 18S primers Fwd 5'-CGGCTACCACATCCAAGGAA, Rev 5'-CCCCGCGAGCACAGA (Sigma) were used for qRT-PCR with Light Cycler 480 SYBER Green I Master Mix (Roche). Reaction mixtures were prepared according to the manufacturer's instructions. Reaction steps: 95° C. 15 min and 40 cycles of 95° C. 15 sec, 60° C. 30 sec and 72° C. 10 sec. PCR was performed in a LightCycler 480 II (Roche) instrument and the ΔΔ Ct method was used to calculate the results. Relative quantities of mRNAs were normalized to 18S mRNA.

Lipid Analysis

Cells were harvested in 2% NaCl solution and lipids were extracted as described in Bligh and Dyer (1959). Lipids corresponding to equal amount of protein per sample were separated by thin-layer chromatography using hexane:diethyl ether:acetic acid, 80:20:1 as the running solvent. The TLC plate was charred and free cholesterol and cholesterol ester bands were quantitated using ImageJ.

Results

Recombinant Hsp70 Stimulates the Removal of Cholesterol from Primary Human Macrophage Foam Cells Differentiated macrophages were incubated with acLDL for 3 days to generate cholesterol loaded foam cells, and then incubated in complete medium (RPMI containing 10% FBS) for 12 h to induce cholesterol removal (efflux) from cells to serum acceptors. To assess the effect of rHsp70 on cholesterol efflux, acLDL loaded cells were pretreated with rHsp70 for 16 h during the last day of loading, followed by continued incubation in the presence of rHsp70 during the 12 h efflux. Cells were then harvested for lipid analysis.

Figure 1:
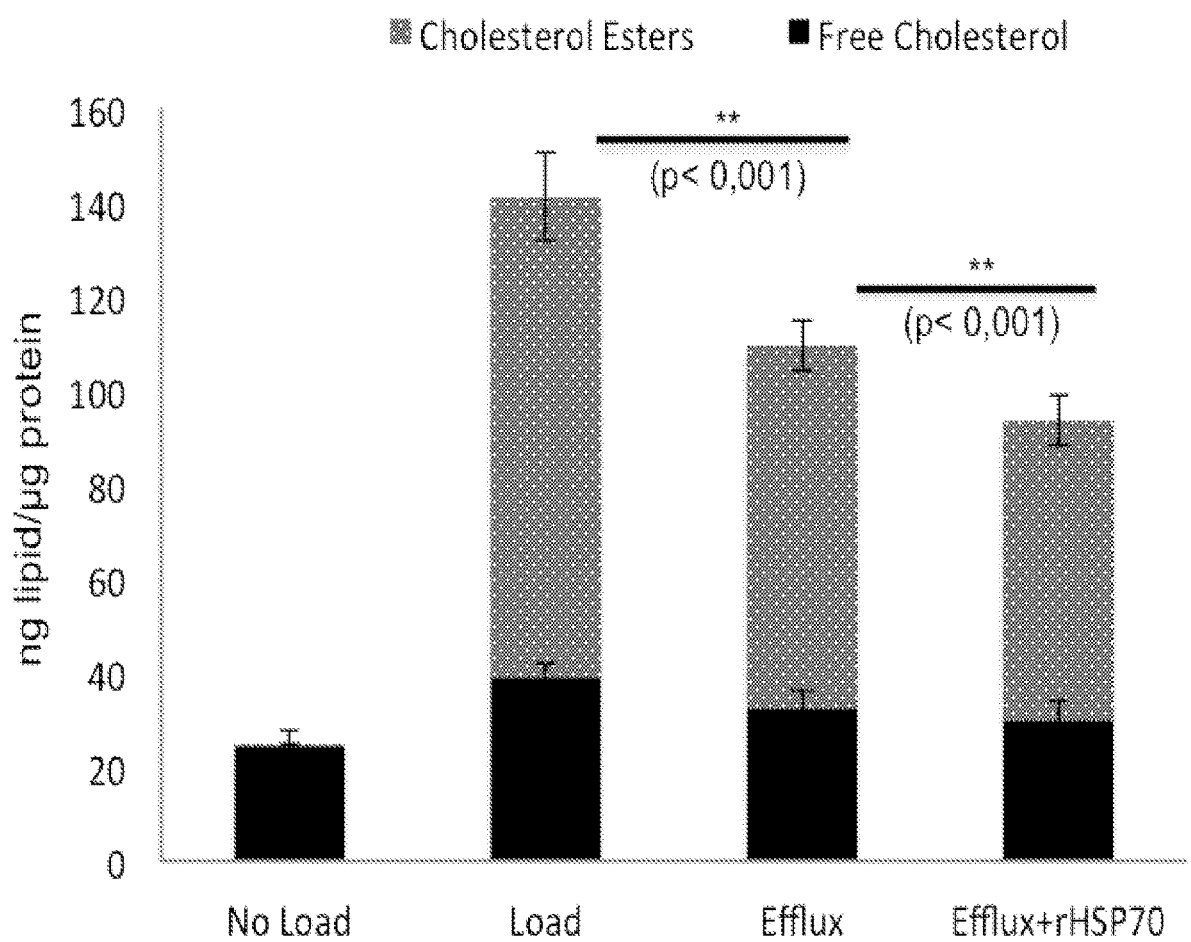
FIG. 1 rHSP70 stimulates the removal of cholesterol from primary human macrophage foam cells. Differentiated human macrophages were loaded with acLDL (50 µg/mL)

Our results demonstrate that acLDL loading in primary human macrophages caused cholesteryl ester deposition compared to control (no load), as expected. Cholesterol efflux to complete medium resulted in decreased cholesterol ester levels, indicating that the cells are able to unload their cholesterol stores. Remarkably, cholesterol removal during the 12 h efflux was significantly enhanced in the presence of rHSP70 (FIG. 1).

Recombinant Hsp70 Increases ABCA1 Transcript and Protein Levels in Primary Human Macrophage Foam Cells A key gatekeeper of cholesterol removal from macrophage foam cells is the ATP-binding cassette transporter A1 (ABCA1) (Wang, S. and Smith, J. D., 2014). It is induced in macrophages upon modified lipoprotein loading and is maintained at high levels during efflux (see FIG. 2, no load vs. load, efflux). ABCA1-dependent cholesterol removal is a rate-limiting factor in high-density lipoprotein (HDL) biogenesis and in the process in reverse cholesterol transport (i.e. removal of cholesterol from tissues and return via circulation via HDL carriers to the liver for excretion). We therefore investigated whether rHsp70-mediated cholesterol efflux involves ABCA1 upregulation.

Figure 2A:
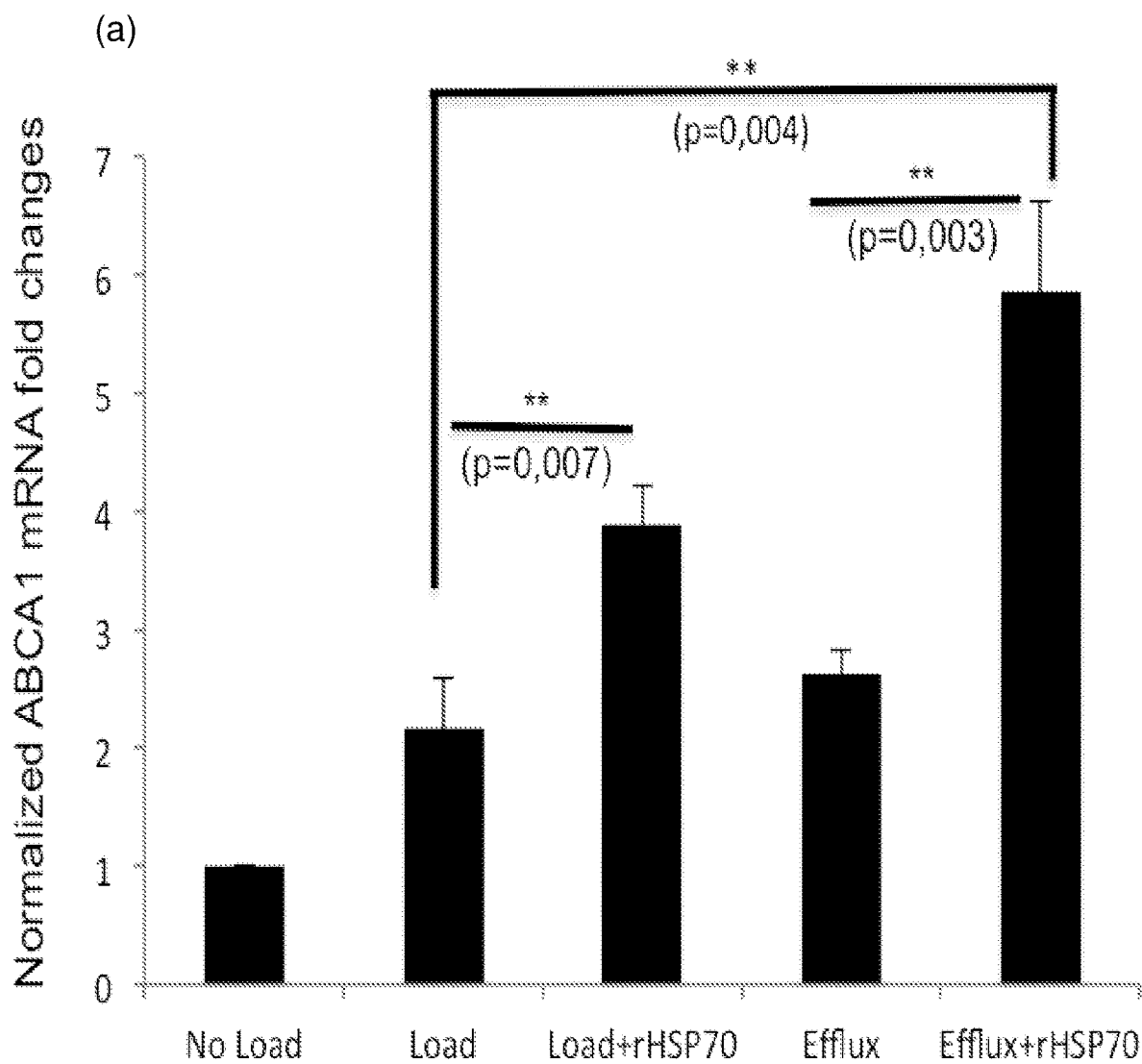
Figure 2B:
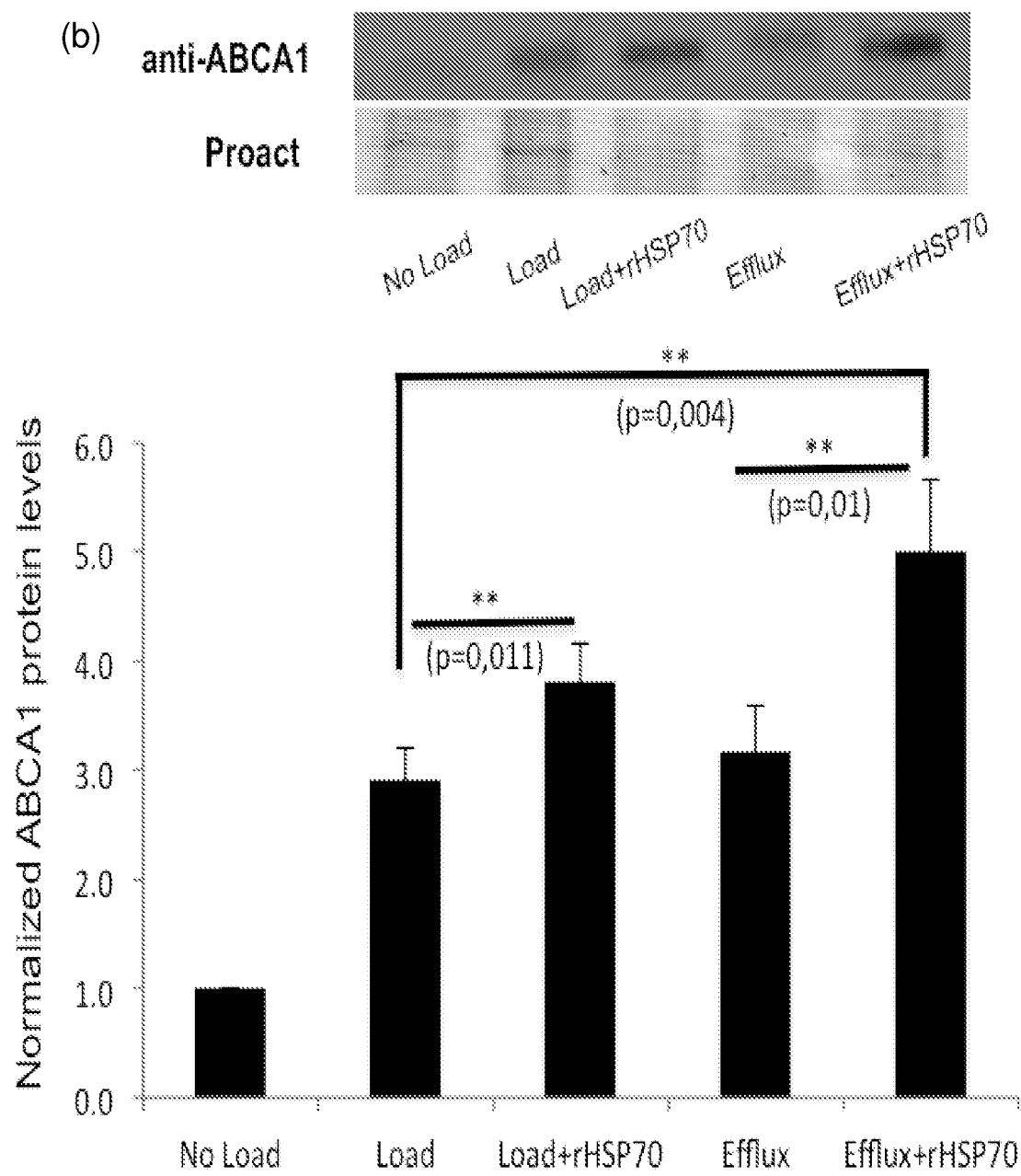

Cells were treated as described above and harvested for transcript and protein analysis. We found a significant increase in the ABCA1 transcript and protein levels upon rHSP70 treatment, both during cholesterol loading and efflux (FIGS. 2a and 2b). Considering the important role of ABCA1 in cholesterol removal, this is likely to be relevant for the mechanism by which rHSP70 acts to facilitate foam cell reversal.

rHSP70 speeds up BODIPY-cholesterol efflux from primarymurine macrophage foam cells. Primary murine bone marrow macrophage foam cells were incubated with BODIPYcholesteryl linoleate-LDL particles. Cholesterol efflux was performed for 24 h to 6% HDL enriched serum in the presence or absence of rHSP70. Results are shown in FIG. 4.

Effect of rHsp70 on the transcript and protein levels of LXR targets in primary human macrophage foam cellsMacrophage foam cells from 4 individual blood donors were incubated −/+rHSP70 during cholesterol efflux and RNAs were extracted. RNA sequencing was performed by Illumina NextSeq sequencer. RNASeq results were analysed using "Gene Set Enrichment Analysis". A major transcriptional re-programming of a number of targets, in particular LXR targets such as ABCA1, FABP4 and GRAMD1A, was induced by rHSP70, as shown in FIG. 5. These changes can also be seen at the protein level (FIG. 6).

Acid Sphingomyelinase Activation is not Involved in Recombinant Hsp70-Mediated Cholesterol Removal from Primary Human Macrophage Foam Cells rHSP70 was reported to stabilize and enhance the activity of acid sphingomyelinase (ASMase) via binding to bis-monoacylglycerophosphate (BMP), a cofactor of this enzyme (Mahalka, A. K. et al, 2014). We therefore tested whether the effect of rHSP70 on cholesterol efflux was mediated through its BMP binding. To this end, the effect of a mutant rHSP70 (W90F rHSP70; mut rHSP70) incapable of interacting with BMP was compared to that of wild-type rHsp70. Our results revealed that the mut rHSP70 produced a similar enhancement of cholesterol efflux as the wt rHSP70 (FIG. 3). This argues that the mechanism by which rHsp70 promotes cholesterol removal in macrophage foam cells is distinct from that involved in rHsp70 mediated reversal of lysosomal pathology in Niemann-Pick disease.

Finally, we investigated whether a higher dosage of rHSP70 improves the cholesterol efflux promoting effect of rHSP70. For this, 200 ug/ml of both wt and mut rHSP70 was applied on human macrophage foam cells before and during cholesterol efflux for 12 h to compare with the effect of 20 ug/ml wt and mut rHSP70 on Chol reversal (FIG. 3).

This was found not to be the case (FIG. 3), suggesting that rHSP70 acts in cholesterol removal via a saturable mechanism.

REFERENCES

Bligh, E. G. and Dyer, W. J., Can. J. Biochem. Physiol. 37, 911-917 (1959)
Blom, T. et al, Circ. Res. 106, 720-9 (2010)
Boyum, A., Nature 204, 793-794 (1964)
Mahalka, A. K. et al. BBA 1838, 1344-1361 (2014).
Wang, S. and Smith, J. D., Biofactors 40, 547-54 (2014)

The invention claimed is:

1. A method for treatment of Smith-Lemli-Opitz Syndrome (SLOS) in a subject, said method comprising administering a bioactive agent selected from the group consisting of: a hydroxylamine derivative small molecule; and Hsp70 protein, or a functional fragment of Hsp70 protein, or a functional variant of Hsp70 protein; to the subject, thereby treating said subject.

2. The method according to claim 1, wherein the hydroxylamine derivative small molecule is selected from the group consisting of: N-[2-hydroxy-3-(1-piperidinyl)-propoxy]-pyridine-1-oxide-3-carboximidoyl chloride (arimoclomol), a stereoisomer thereof, an acid addition salt of arimoclomol, and an acid addition salt of a stereoisomer of arimoclomol.

3. The method according to claim 1, wherein the hydroxylamine derivative small molecule is selected from the group consisting of:
   a. a racemate of N-[2-hydroxy-3-(1-piperidinyl)-propoxy]-pyridine-1-oxide-3-carboximidoyl chloride,
   b. an optically active stereoisomer of N-[2-hydroxy-3-(1-piperidinyl)-propoxy]-pyridine-1-oxide-3-carboximidoyl chloride,
   c. an enantiomer of N-[2-hydroxy-3-(1-piperidinyl)-propoxy]-pyridine-1-oxide-3-carboximidoyl chloride,
   d. (+)—R—N-[2-hydroxy-3-(1-piperidinyl)-propoxy]-pyridine-1-oxide-3-carboximidoyl chloride and (−)—(S)—N-[2-hydroxy-3-(1-piperidinyl)-propoxy]-pyridine-1-oxide-3-carboximidoyl chloride,
   e. an acid addition salt of N-[2-hydroxy-3-(1-piperidinyl)-propoxy]-pyridine-1-oxide-3-carboximidoyl chloride,
   f. N-[2-hydroxy-3-(1-piperidinyl)-propoxy]-pyridine-1-oxide-3-carboximidoyl chloride citrate (BRX-345), and N-[2-hydroxy-3-(1-piperidinyl)-propoxy]-pyridine-1-oxide-3-carboximidoyl chloride maleate, and
   g. (+)—R—N-[2-hydroxy-3-(1-piperidinyl)-propoxy]-pyridine-1-oxide-3-carboximidoyl chloride citrate; (−)—S—N-[2-hydroxy-3-(1-piperidinyl)-propoxy]-pyridine-1-oxide-3-carboximidoyl chloride citrate; (+)—R—N-[2-hydroxy-3-(1-piperidinyl)-propoxy]-pyridine-1-oxide-3-carboximidoyl chloride maleate; and (−)—S—N-[2-hydroxy-3-(1-piperidinyl)-propoxy]-pyridine-1-oxide-3-carboximidoyl chloride maleate.

4. The method according to claim 1, wherein the hydroxylamine derivative small molecule is selected from the group consisting of:
   a. N-[2-hydroxy-3-(1-piperidinyl)-propoxy]-pyridine-1-oxide-3-carboximidoyl chloride (arimoclomol), a stereoisomer, or an acid addition salt thereof,
   b. N-[2-hydroxy-3-(1-piperidinyl)propoxy]-3-pyridinecarboximidamide dihydrochloride (BGP-15), a stereoisomer, or an acid addition salt thereof, c. N-[2-hydroxy-3-(1-piperidinyl)-propoxy]-3-pyridinecarboximidoyl chloride (bimoclomol), a stereoisomer, or an acid addition salt thereof, and d. 5,6-dihydro-5-(1-piperidinyl)methyl-3-(3-pyridyl)-4H-1,2,4-oxadiazine (iroxanadine), a stereoisomer, or an acid addition salt thereof.

5. The method according to claim 1, wherein the hydroxylamine derivative small molecule is selected from the group consisting of:

a. a racemate of 5,6-dihydro-5-(1-piperidinyl)methyl-3-(3-pyridyl)-4H-1,2,4-oxadiazine, b. an optically active stereoisomer of 5,6-dihydro-5-(1-piperidinyl)methyl-3-(3-pyridyl)-4H-1,2,4-oxadiazine, c. an enantiomer of 5,6-dihydro-5-(1-piperidinyl)methyl-3-(3-pyridyl)-4H-1,2,4-oxadiazine, d. (+)-5,6-dihydro-5-(1-piperidinyl)methyl-3-(3-pyridyl)-4H-1,2,4-oxadiazine and (−)-5,6-dihydro-5-(1-piperidinyl)methyl-3-(3-pyridyl)-4H-1,2,4-oxadiazine, e. an acid addition salt of 5,6-dihydro-5-(1-piperidinyl)methyl-3-(3-pyridyl)-4H-1,2,4-oxadiazine, f. 5,6-dihydro-5-(1-piperidinyl)methyl-3-(3-pyridyl)-4H-1,2,4-oxadiazine citrate, and 5,6-dihydro-5-(1-piperidinyl)methyl-3-(3-pyridyl)-4H-1,2,4-oxadiazine maleate, and g. (+)-5,6-dihydro-5-(1-piperidinyl)methyl-3-(3-pyridyl)-4H-1,2,4-oxadiazine citrate; (−)-5,6-dihydro-5-(1-piperidinyl)methyl-3-(3-pyridyl)-4H-1,2,4-oxadiazine citrate; (+)-5,6-dihydro-5-(1-piperidinyl)methyl-3-(3-pyridyl)-4H-1,2,4-oxadiazine maleate; and (−)-5,6-dihydro-5-(1-piperidinyl)methyl-3-(3-pyridyl)-4H-1,2,4-oxadiazine maleate.

6. The method according to claim 1, wherein the hydroxylamine derivative small molecule is selected from the group consisting of:

a. a racemate of N-[2-hydroxy-3-(1-piperidinyl)-propoxy]-3-pyridinecarboximidoyl chloride, b. an optically active stereoisomer of N-[2-hydroxy-3-(1-piperidinyl)-propoxy]-3-pyridinecarboximidoyl chloride, c. an enantiomer of N-[2-hydroxy-3-(1-piperidinyl)-propoxy]-3-pyridine-carboximidoyl chloride, d. (+)—R—N-[2-hydroxy-3-(1-piperidinyl)-propoxy]-3-pyridinecarboximidoyl chloride and (−)—(S)—N-[2-hydroxy-3-(1-piperidinyl)-propoxy]-3-pyridinecarboximidoyl chloride, e. an acid addition salt of N-[2-hydroxy-3-(1-piperidinyl)-propoxy]-3-pyridinecarboximidoyl chloride, f. N-[2-hydroxy-3-(1-piperidinyl)-propoxy]-3-pyridinecarboximidoyl chloride citrate, and N-[2-hydroxy-3-(1-piperidinyl)-propoxy]-3-pyridinecarboximidoyl chloride maleate, and g. (+)—R—N-[2-hydroxy-3-(1-piperidinyl)-propoxy]-3-pyridinecarboximidoyl chloride citrate; (−)—S—N-[2-hydroxy-3-(1-piperidinyl)-propoxy]-3-pyridinecarboximidoyl chloride citrate; (+)—R—N-[2-hydroxy-3-(1-piperidinyl)-propoxy]-3-pyridinecarboximidoyl chloride maleate; and (−)—S—N-[2-hydroxy-3-(1-piperidinyl)-propoxy]-3-pyridinecarboximidoyl chloride maleate.

7. The method according to claim 1, wherein said Hsp70 protein is selected from the group consisting of: HSPA1A (SEQ ID NO:1 and SEQ ID NO:2), HSPA1B (SEQ ID NO:4 and SEQ ID NO:5), a functional fragment of any thereof, and a functional variant of any thereof.

8. The method according to claim 1, wherein the functional variant of Hsp70 has at least 90% identity to an Hsp70 protein selected from the group consisting of: HSPA1A (SEQ ID NOs:1 and 2), HSPA1B (SEQ ID NOs: 4 and 5), and a fragment of any thereof.

9. The method according to claim 1, wherein said Hsp70 protein is recombinant Hsp70 (rHsp70).

10. The method according to claim 1, wherein said functional variant of Hsp70 is a naturally occurring variant, or a fragment of a naturally occurring variant, of Hsp70.

11. A method for one or more of:

i. stimulating cholesterol efflux from macrophages, ii. stimulating the decrease of cholesterol esters in macrophages, iii. facilitating cholesterol reduction during macrophage foam cell reversal, iv. reducing intracellular cholesterol in macrophages, v. increasing or stimulating ABCA1 levels or activity, vi. increasing or stimulating ABCA1-protein levels or activity, and vii. increasing or stimulating ABCA1-mRNA levels or activity;

in a subject, said method comprising administering a bioactive agent selected from the group consisting of: a hydroxylamine derivative small molecule; Hsp70 protein, or a functional fragment or functional variant thereof to the subject, thereby achieving one or more of i. to vi.

12. The method according to claim 1, wherein said functional fragment of Hsp70 comprises or consists of at least 150 contiguous amino acids derived from Hsp70.

\* \* \* \* \*

SEQUENCE LISTING

```
<160> NUMBER OF SEQ ID NOS: 6

<210> SEQ ID NO 1
<211> LENGTH: 641
<212> TYPE: PRT
<213> ORGANISM: Homo sapiens

<400> SEQUENCE: 1

Met Ala Lys Ala Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80
```

```
Pro Val Val Gln Ser Asp Met Lys His Trp Pro Phe Gln Val Ile Asn
                85                  90                  95
Asp Gly Asp Lys Pro Lys Val Gln Val Ser Tyr Lys Gly Glu Thr Lys
            100                 105                 110
Ala Phe Tyr Pro Glu Glu Ile Ser Ser Met Val Leu Thr Lys Met Lys
        115                 120                 125
Glu Ile Ala Glu Ala Tyr Leu Gly Tyr Pro Val Thr Asn Ala Val Ile
    130                 135                 140
Thr Val Pro Ala Tyr Phe Asn Asp Ser Gln Arg Gln Ala Thr Lys Asp
145                 150                 155                 160
Ala Gly Val Ile Ala Gly Leu Asn Val Leu Arg Ile Ile Asn Glu Pro
                165                 170                 175
Thr Ala Ala Ala Ile Ala Tyr Gly Leu Asp Arg Thr Gly Lys Gly Glu
            180                 185                 190
Arg Asn Val Leu Ile Phe Asp Leu Gly Gly Gly Thr Phe Asp Val Ser
        195                 200                 205
Ile Leu Thr Ile Asp Asp Gly Ile Phe Glu Val Lys Ala Thr Ala Gly
    210                 215                 220
Asp Thr His Leu Gly Gly Glu Asp Phe Asp Asn Arg Leu Val Asn His
225                 230                 235                 240
Phe Val Glu Glu Phe Lys Arg Lys His Lys Lys Asp Ile Ser Gln Asn
                245                 250                 255
Lys Arg Ala Val Arg Arg Leu Arg Thr Ala Cys Glu Arg Ala Lys Arg
            260                 265                 270
Thr Leu Ser Ser Ser Thr Gln Ala Ser Leu Glu Ile Asp Ser Leu Phe
        275                 280                 285
Glu Gly Ile Asp Phe Tyr Thr Ser Ile Thr Arg Ala Arg Phe Glu Glu
    290                 295                 300
Leu Cys Ser Asp Leu Phe Arg Ser Thr Leu Glu Pro Val Glu Lys Ala
305                 310                 315                 320
Leu Arg Asp Ala Lys Leu Asp Lys Ala Gln Ile His Asp Leu Val Leu
                325                 330                 335
Val Gly Gly Ser Thr Arg Ile Pro Lys Val Gln Lys Leu Leu Gln Asp
            340                 345                 350
Phe Phe Asn Gly Arg Asp Leu Asn Lys Ser Ile Asn Pro Asp Glu Ala
        355                 360                 365
Val Ala Tyr Gly Ala Ala Val Gln Ala Ala Ile Leu Met Gly Asp Lys
    370                 375                 380
Ser Glu Asn Val Gln Asp Leu Leu Leu Leu Asp Val Ala Pro Leu Ser
385                 390                 395                 400
Leu Gly Leu Glu Thr Ala Gly Gly Val Met Thr Ala Leu Ile Lys Arg
                405                 410                 415
Asn Ser Thr Ile Pro Thr Lys Gln Thr Gln Ile Phe Thr Thr Tyr Ser
            420                 425                 430
Asp Asn Gln Pro Gly Val Leu Ile Gln Val Tyr Glu Gly Glu Arg Ala
        435                 440                 445
Met Thr Lys Asp Asn Asn Leu Leu Gly Arg Phe Glu Leu Ser Gly Ile
    450                 455                 460
Pro Pro Ala Pro Arg Gly Val Pro Gln Ile Glu Val Thr Phe Asp Ile
465                 470                 475                 480
Asp Ala Asn Gly Ile Leu Asn Val Thr Ala Thr Asp Lys Ser Thr Gly
                485                 490                 495
Lys Ala Asn Lys Ile Thr Ile Thr Asn Asp Lys Gly Arg Leu Ser Lys
```

```
                500             505             510
Glu Glu Ile Glu Arg Met Val Gln Glu Ala Glu Lys Tyr Lys Ala Glu
            515                 520                 525
Asp Glu Val Gln Arg Glu Arg Val Ser Ala Lys Asn Ala Leu Glu Ser
            530                 535                 540
Tyr Ala Phe Asn Met Lys Ser Ala Val Glu Asp Gly Leu Lys Gly
545                 550                 555                 560
Lys Ile Ser Glu Ala Asp Lys Lys Val Leu Asp Lys Cys Gln Glu
                565                 570                 575
Val Ile Ser Trp Leu Asp Ala Asn Thr Leu Ala Glu Lys Asp Glu Phe
            580                 585                 590
Glu His Lys Arg Lys Glu Leu Glu Gln Val Cys Asn Pro Ile Ile Ser
            595                 600                 605
Gly Leu Tyr Gln Gly Ala Gly Gly Pro Gly Pro Gly Gly Phe Gly Ala
            610                 615                 620
Gln Gly Pro Lys Gly Gly Ser Gly Ser Gly Pro Thr Ile Glu Glu Val
625                 630                 635                 640
Asp

<210> SEQ ID NO 2
<211> LENGTH: 640
<212> TYPE: PRT
<213> ORGANISM: Homo sapiens

<400> SEQUENCE: 2

Ala Lys Ala Ala Ala Ile Gly Ile Asp Leu Gly Thr Thr Tyr Ser Cys
1               5                   10                  15
Val Gly Val Phe Gln His Gly Lys Val Glu Ile Ile Ala Asn Asp Gln
            20                  25                  30
Gly Asn Arg Thr Thr Pro Ser Tyr Val Ala Phe Thr Asp Thr Glu Arg
        35                  40                  45
Leu Ile Gly Asp Ala Ala Lys Asn Gln Val Ala Leu Asn Pro Gln Asn
    50                  55                  60
Thr Val Phe Asp Ala Lys Arg Leu Ile Gly Arg Lys Phe Gly Asp Pro
65                  70                  75                  80
Val Val Gln Ser Asp Met Lys His Trp Pro Phe Gln Val Ile Asn Asp
                85                  90                  95
Gly Asp Lys Pro Lys Val Gln Val Ser Tyr Lys Gly Glu Thr Lys Ala
            100                 105                 110
Phe Tyr Pro Glu Glu Ile Ser Ser Met Val Leu Thr Lys Met Lys Glu
        115                 120                 125
Ile Ala Glu Ala Tyr Leu Gly Tyr Pro Val Thr Asn Ala Val Ile Thr
    130                 135                 140
Val Pro Ala Tyr Phe Asn Asp Ser Gln Arg Gln Ala Thr Lys Asp Ala
145                 150                 155                 160
Gly Val Ile Ala Gly Leu Asn Val Leu Arg Ile Ile Asn Glu Pro Thr
                165                 170                 175
Ala Ala Ala Ile Ala Tyr Gly Leu Asp Arg Thr Gly Lys Gly Glu Arg
            180                 185                 190
Asn Val Leu Ile Phe Asp Leu Gly Gly Gly Thr Phe Asp Val Ser Ile
        195                 200                 205
Leu Thr Ile Asp Asp Gly Ile Phe Glu Val Lys Ala Thr Ala Gly Asp
    210                 215                 220
Thr His Leu Gly Gly Glu Asp Phe Asp Asn Arg Leu Val Asn His Phe
```

```
            225                 230                 235                 240
Val Glu Glu Phe Lys Arg Lys His Lys Lys Asp Ile Ser Gln Asn Lys
                    245                 250                 255

Arg Ala Val Arg Arg Leu Arg Thr Ala Cys Glu Arg Ala Lys Arg Thr
                260                 265                 270

Leu Ser Ser Ser Thr Gln Ala Ser Leu Glu Ile Asp Ser Leu Phe Glu
                275                 280                 285

Gly Ile Asp Phe Tyr Thr Ser Ile Thr Arg Ala Arg Phe Glu Glu Leu
            290                 295                 300

Cys Ser Asp Leu Phe Arg Ser Thr Leu Glu Pro Val Glu Lys Ala Leu
305                 310                 315                 320

Arg Asp Ala Lys Leu Asp Lys Ala Gln Ile His Asp Leu Val Leu Val
                    325                 330                 335

Gly Gly Ser Thr Arg Ile Pro Lys Val Gln Lys Leu Leu Gln Asp Phe
                340                 345                 350

Phe Asn Gly Arg Asp Leu Asn Lys Ser Ile Asn Pro Asp Glu Ala Val
                355                 360                 365

Ala Tyr Gly Ala Ala Val Gln Ala Ala Ile Leu Met Gly Asp Lys Ser
            370                 375                 380

Glu Asn Val Gln Asp Leu Leu Leu Leu Asp Val Ala Pro Leu Ser Leu
385                 390                 395                 400

Gly Leu Glu Thr Ala Gly Gly Val Met Thr Ala Leu Ile Lys Arg Asn
                    405                 410                 415

Ser Thr Ile Pro Thr Lys Gln Thr Gln Ile Phe Thr Thr Tyr Ser Asp
                420                 425                 430

Asn Gln Pro Gly Val Leu Ile Gln Val Tyr Glu Gly Glu Arg Ala Met
            435                 440                 445

Thr Lys Asp Asn Asn Leu Leu Gly Arg Phe Glu Leu Ser Gly Ile Pro
            450                 455                 460

Pro Ala Pro Arg Gly Val Pro Gln Ile Glu Val Thr Phe Asp Ile Asp
465                 470                 475                 480

Ala Asn Gly Ile Leu Asn Val Thr Ala Thr Asp Lys Ser Thr Gly Lys
                    485                 490                 495

Ala Asn Lys Ile Thr Ile Thr Asn Asp Lys Gly Arg Leu Ser Lys Glu
                500                 505                 510

Glu Ile Glu Arg Met Val Gln Glu Ala Glu Lys Tyr Lys Ala Glu Asp
            515                 520                 525

Glu Val Gln Arg Glu Arg Val Ser Ala Lys Asn Ala Leu Glu Ser Tyr
            530                 535                 540

Ala Phe Asn Met Lys Ser Ala Val Glu Asp Glu Gly Leu Lys Gly Lys
545                 550                 555                 560

Ile Ser Glu Ala Asp Lys Lys Lys Val Leu Asp Lys Cys Gln Glu Val
                    565                 570                 575

Ile Ser Trp Leu Asp Ala Asn Thr Leu Ala Glu Lys Asp Glu Phe Glu
                580                 585                 590

His Lys Arg Lys Glu Leu Glu Gln Val Cys Asn Pro Ile Ile Ser Gly
            595                 600                 605

Leu Tyr Gln Gly Ala Gly Gly Pro Gly Pro Gly Gly Phe Gly Ala Gln
            610                 615                 620

Gly Pro Lys Gly Gly Ser Gly Ser Gly Pro Thr Ile Glu Glu Val Asp
625                 630                 635                 640

<210> SEQ ID NO 3
```

<211> LENGTH: 2445
<212> TYPE: DNA
<213> ORGANISM: Homo sapiens

<400> SEQUENCE: 3

| | | | | | |
|---|---|---|---|---|---|
| ataaaagccc | aggggcaagc | ggtccggata | acggctagcc | tgaggagctg | ctgcgacagt | 60 |
| ccactacctt | tttcgagagt | gactcccgtt | gtcccaaggc | ttcccagagc | gaacctgtgc | 120 |
| ggctgcaggc | accggcgcgt | cgagtttccg | gcgtccggaa | ggaccgagct | cttctcgcgg | 180 |
| atccagtgtt | ccgtttccag | cccccaatct | cagagcggag | ccgacagaga | gcagggaacc | 240 |
| ggcatggcca | agccgcggc | gatcggcatc | gacctgggca | ccacctactc | ctgcgtgggg | 300 |
| gtgttccaac | acggcaaggt | ggagatcatc | gccaacgacc | agggcaaccg | caccacccc | 360 |
| agctacgtgg | ccttcacgga | caccgagcgg | ctcatcgggg | atgcggccaa | gaaccaggtg | 420 |
| gcgctgaacc | gcagaacac | cgtgtttgac | gcgaagcggc | tgattggccg | caagttcggc | 480 |
| gacccggtgg | tgcagtcgga | catgaagcac | tggccttcc | aggtgatcaa | cgacggagac | 540 |
| aagcccaagg | tgcaggtgag | ctacaagggg | gagaccaagg | cattctaccc | cgaggagatc | 600 |
| tcgtccatgg | tgctgaccaa | gatgaaggag | atcgccgagg | cgtacctggg | ctacccggtg | 660 |
| accaacgcgg | tgatcaccgt | gccggcctac | ttcaacgact | cgcagcgcca | ggccaccaag | 720 |
| gatgcgggtg | tgatcgcggg | gctcaacgtg | ctgcggatca | tcaacgagcc | cacggccgcc | 780 |
| gccatcgcct | acgcctgga | cagaacgggc | aaggggagc | gcaacgtgct | catctttgac | 840 |
| ctgggcgggg | gcaccttcga | cgtgtccatc | ctgacgatcg | acgacggcat | cttcgaggtg | 900 |
| aaggccacgg | ccggggacac | ccacctgggt | ggggaggact | tgacaacag | gctggtgaac | 960 |
| cacttcgtgg | aggagttcaa | gagaaaacac | aagaaggaca | tcagccagaa | caagcgagcc | 1020 |
| gtgaggcggc | tgcgcaccgc | ctgcgagagg | gccaagagga | ccctgtcgtc | cagcacccag | 1080 |
| gccagcctgg | agatcgactc | cctgtttgag | ggcatcgact | tctacacgtc | catcaccagg | 1140 |
| gcgaggttcg | aggagctgtg | ctccgacctg | ttccgaagca | ccctggagcc | cgtggagaag | 1200 |
| gctctgcgcg | acgccaagct | ggacaaggcc | cagattcacg | acctggtcct | ggtcggggc | 1260 |
| tccacccgca | tccccaaggt | gcagaagctg | ctgcaggact | tcttcaacgg | gcgcgacctg | 1320 |
| aacaagagca | tcaaccccga | cgaggctgtg | gcctacgggg | cggcggtgca | ggcggccatc | 1380 |
| ctgatggggg | acaagtccga | gaacgtgcag | gacctgctgc | tgctggacgt | ggctcccctg | 1440 |
| tcgctggggc | tggagacggc | cggaggcgtg | atgactgccc | tgatcaagcg | caactccacc | 1500 |
| atccccacca | gcagacgca | gatcttcacc | acctactccg | acaaccaacc | cggggtgctg | 1560 |
| atccaggtgt | acgagggcga | gagggccatg | acgaaagaca | caatctgtt | ggggcgcttc | 1620 |
| gagctgagcg | gcatccctcc | ggcccccagg | ggcgtgcccc | agatcgaggt | gaccttcgac | 1680 |
| atcgatgcca | acggcatcct | gaacgtcacg | gccacggaca | agagcaccgg | caaggccaac | 1740 |
| aagatcacca | tcaccaacga | caagggccgc | ctgagcaagg | aggagatcga | gcgcatggtg | 1800 |
| caggaggcgg | agaagtacaa | agcggaggac | gaggtgcagc | gcgagagggt | gtcagccaag | 1860 |
| aacgccctgg | agtcctacgc | cttcaacatg | aagagcgccg | tggaggatga | ggggctcaag | 1920 |
| ggcaagatca | gcgaggcgga | caagaagaag | gtgctggaca | agtgtcaaga | ggtcatctcg | 1980 |
| tggctggacg | ccaacaccct | tggccgagaag | gacgagtttg | agcacaagag | gaaggagctg | 2040 |
| gagcaggtgt | gtaaccccat | catcagcgga | ctgtaccagg | gtgccggtgg | tcccgggcct | 2100 |
| gggggcttcg | ggctcagggg | tcccaaggga | gggtctgggt | caggccccac | cattgaggag | 2160 |
| gtagattagg | ggcctttcca | agattgctgt | ttttgttttg | gagcttcaag | actttgcatt | 2220 |

```
tcctagtatt tctgtttgtc agttctcaat ttcctgtgtt tgcaatgttg aaattttttg    2280
gtgaagtact gaacttgctt ttttccggt ttctacatgc agagatgaat ttatactgcc     2340
atcttacgac tatttcttct ttttaataca cttaactcag gccatttttt aagttggtta    2400
cttcaaagta ataaacttt aaaattcaaa aaaaaaaaaa aaaaa                     2445

<210> SEQ ID NO 4
<211> LENGTH: 641
<212> TYPE: PRT
<213> ORGANISM: Homo sapiens

<400> SEQUENCE: 4

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
            20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
    50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335
```

```
Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365

Val Ala Tyr Gly Ala Ala Val Gln Ala Ala Ile Leu Met Gly Asp Lys
    370                 375                 380

Ser Glu Asn Val Gln Asp Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Arg Phe Glu Leu Ser Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
            500                 505                 510

Glu Glu Ile Glu Arg Met Val Gln Glu Ala Glu Lys Tyr Lys Ala Glu
        515                 520                 525

Asp Glu Val Gln Arg Glu Arg Val Ser Ala Lys Asn Ala Leu Glu Ser
    530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
        595                 600                 605

Gly Leu Tyr Gln Gly Ala Gly Gly Pro Gly Pro Gly Gly Phe Gly Ala
    610                 615                 620

Gln Gly Pro Lys Gly Gly Ser Gly Ser Gly Pro Thr Ile Glu Glu Val
625                 630                 635                 640

Asp

<210> SEQ ID NO 5
<211> LENGTH: 640
<212> TYPE: PRT
<213> ORGANISM: Homo sapiens

<400> SEQUENCE: 5

Ala Lys Ala Ala Ala Ile Gly Ile Asp Leu Gly Thr Thr Tyr Ser Cys
1               5                   10                  15

Val Gly Val Phe Gln His Gly Lys Val Glu Ile Ile Ala Asn Asp Gln
                20                  25                  30

Gly Asn Arg Thr Thr Pro Ser Tyr Val Ala Phe Thr Asp Thr Glu Arg
            35                  40                  45

Leu Ile Gly Asp Ala Ala Lys Asn Gln Val Ala Leu Asn Pro Gln Asn
        50                  55                  60
```

```
Thr Val Phe Asp Ala Lys Arg Leu Ile Gly Arg Lys Phe Gly Asp Pro
 65                  70                  75                  80

Val Val Gln Ser Asp Met Lys His Trp Pro Phe Gln Val Ile Asn Asp
                 85                  90                  95

Gly Asp Lys Pro Lys Val Gln Val Ser Tyr Lys Gly Glu Thr Lys Ala
                100                 105                 110

Phe Tyr Pro Glu Glu Ile Ser Ser Met Val Leu Thr Lys Met Lys Glu
                115                 120                 125

Ile Ala Glu Ala Tyr Leu Gly Tyr Pro Val Thr Asn Ala Val Ile Thr
130                 135                 140

Val Pro Ala Tyr Phe Asn Asp Ser Gln Arg Gln Ala Thr Lys Asp Ala
145                 150                 155                 160

Gly Val Ile Ala Gly Leu Asn Val Leu Arg Ile Ile Asn Glu Pro Thr
                165                 170                 175

Ala Ala Ala Ile Ala Tyr Gly Leu Asp Arg Thr Gly Lys Gly Glu Arg
                180                 185                 190

Asn Val Leu Ile Phe Asp Leu Gly Gly Gly Thr Phe Asp Val Ser Ile
                195                 200                 205

Leu Thr Ile Asp Asp Gly Ile Phe Glu Val Lys Ala Thr Ala Gly Asp
210                 215                 220

Thr His Leu Gly Gly Glu Asp Phe Asp Asn Arg Leu Val Asn His Phe
225                 230                 235                 240

Val Glu Glu Phe Lys Arg Lys His Lys Lys Asp Ile Ser Gln Asn Lys
                245                 250                 255

Arg Ala Val Arg Arg Leu Arg Thr Ala Cys Glu Arg Ala Lys Arg Thr
                260                 265                 270

Leu Ser Ser Ser Thr Gln Ala Ser Leu Glu Ile Asp Ser Leu Phe Glu
                275                 280                 285

Gly Ile Asp Phe Tyr Thr Ser Ile Thr Arg Ala Arg Phe Glu Glu Leu
290                 295                 300

Cys Ser Asp Leu Phe Arg Ser Thr Leu Glu Pro Val Glu Lys Ala Leu
305                 310                 315                 320

Arg Asp Ala Lys Leu Asp Lys Ala Gln Ile His Asp Leu Val Leu Val
                325                 330                 335

Gly Gly Ser Thr Arg Ile Pro Lys Val Gln Lys Leu Leu Gln Asp Phe
                340                 345                 350

Phe Asn Gly Arg Asp Leu Asn Lys Ser Ile Asn Pro Asp Glu Ala Val
                355                 360                 365

Ala Tyr Gly Ala Ala Val Gln Ala Ala Ile Leu Met Gly Asp Lys Ser
                370                 375                 380

Glu Asn Val Gln Asp Leu Leu Leu Leu Asp Val Ala Pro Leu Ser Leu
385                 390                 395                 400

Gly Leu Glu Thr Ala Gly Gly Val Met Thr Ala Leu Ile Lys Arg Asn
                405                 410                 415

Ser Thr Ile Pro Thr Lys Gln Thr Gln Ile Phe Thr Thr Tyr Ser Asp
                420                 425                 430

Asn Gln Pro Gly Val Leu Ile Gln Val Tyr Glu Gly Glu Arg Ala Met
                435                 440                 445

Thr Lys Asp Asn Asn Leu Leu Gly Arg Phe Glu Leu Ser Gly Ile Pro
                450                 455                 460

Pro Ala Pro Arg Gly Val Pro Gln Ile Glu Val Thr Phe Asp Ile Asp
465                 470                 475                 480
```

```
Ala Asn Gly Ile Leu Asn Val Thr Ala Thr Asp Lys Ser Thr Gly Lys
            485                 490                 495

Ala Asn Lys Ile Thr Ile Thr Asn Asp Lys Gly Arg Leu Ser Lys Glu
        500                 505                 510

Glu Ile Glu Arg Met Val Gln Glu Ala Glu Lys Tyr Lys Ala Glu Asp
        515                 520                 525

Glu Val Gln Arg Glu Arg Val Ser Ala Lys Asn Ala Leu Glu Ser Tyr
        530                 535                 540

Ala Phe Asn Met Lys Ser Ala Val Glu Asp Glu Gly Leu Lys Gly Lys
545                 550                 555                 560

Ile Ser Glu Ala Asp Lys Lys Lys Val Leu Asp Lys Cys Gln Glu Val
                565                 570                 575

Ile Ser Trp Leu Asp Ala Asn Thr Leu Ala Glu Lys Asp Glu Phe Glu
                580                 585                 590

His Lys Arg Lys Glu Leu Glu Gln Val Cys Asn Pro Ile Ile Ser Gly
            595                 600                 605

Leu Tyr Gln Gly Ala Gly Gly Pro Gly Pro Gly Phe Gly Ala Gln
        610                 615                 620

Gly Pro Lys Gly Gly Ser Gly Ser Gly Pro Thr Ile Glu Glu Val Asp
625                 630                 635                 640
```

<210> SEQ ID NO 6
<211> LENGTH: 2551
<212> TYPE: DNA
<213> ORGANISM: Homo sapiens

<400> SEQUENCE: 6

```
ggaaaacggc cagcctgagg agctgctgcg agggtccgct tcgtctttcg agagtgactc      60
ccgcggtccc aaggctttcc agagcgaacc tgtgcggctg caggcaccgg cgtgttgagt     120
ttccggcgtt ccgaaggact gagctcttgt cgcggatccc gtccgccgtt ccagccccc      180
agtctcagag cggagcccac agagcagggc accggcatgg ccaaagccgc ggcgatcggc     240
atcgacctgg gcaccaccta ctcctgcgtg ggggtgttcc aacacggcaa ggtggagatc     300
atcgccaacg accagggcaa ccgcaccacc cccagctacg tggccttcac ggacaccgag     360
cggctcatcg gggatgcggc caagaaccag gtggcgctga acccgcagaa caccgtgttt     420
gacgcgaagc ggctgatcgg ccgcaagttc ggcgacccgg tggtgcagtc ggacatgaag     480
cactggcctt tccaggtgat caacgacgga gacaagccca aggtgcaggt gagctacaag     540
ggggagacca aggcattcta ccccgaggag atctcgtcca tggtgctgac caagatgaag     600
gagatcgccg aggcgtacct gggctacccg gtgaccaacg cggtgatcac cgtgccggcc     660
tacttcaacg actcgcagcg ccaggccacc aaggatgcgg tgtgtatcgc ggggctcaac     720
gtgctgcgga tcatcaacga gcccacggcc gccgccatcg cctacggcct ggacagaacg     780
ggcaaggggg agcgcaacgt gctcatcttt gacctgggcg ggggcacctt cgacgtgtcc     840
atcctgacga tcgacgacgg catcttcgag gtgaaggcca cggccgggga cacccacctg     900
ggtggggagg actttgacaa caggctggtg aaccacttcg tggaggagtt caagagaaaa     960
cacaagaagg acatcagcca gaacaagcga gccgtgaggc ggctgcgcac cgcctgcgag    1020
agggccaaga ggaccctgtc gtccagcacc caggccagcc tggagatcga ctccctgttt    1080
gagggcatcg acttctacac gtccatcacc agggcgaggt tcgaggagct gtgctccgac    1140
ctgttccgaa gcaccctgga gcccgtggag aaggctctgc gcgacgccaa gctggacaag    1200
gcccagattc acgacctggt cctggtcggg ggctccaccc gcatccccaa ggtgcagaag    1260
```

-continued

```
ctgctgcagg acttcttcaa cgggcgcgac ctgaacaaga gcatcaaccc cgacgaggct    1320
gtggcctacg gggcggcggt gcaggcggcc atcctgatgg gggacaagtc cgagaacgtg    1380
caggacctgc tgctgctgga cgtggctccc ctgtcgctgg ggctggagac ggccggaggc    1440
gtgatgactg ccctgatcaa gcgcaactcc accatcccca ccaagcagac gcagatcttc    1500
accacctact ccgacaacca acccggggtg ctgatccagg tgtacgaggg cgagagggcc    1560
atgacgaaag acaacaatct gttggggcgc ttcgagctga gcggcatccc tccggccccc    1620
aggggcgtgc cccagatcga ggtgaccttc gacatcgatg ccaacggcat cctgaacgtc    1680
acggccacgg acaagagcac cggcaaggcc aacaagatca ccatcaccaa cgacaagggc    1740
cgcctgagca aggaggagat cgagcgcatg gtgcaggagg cggagaagta caaagcggag    1800
gacgaggtgc agcgcgagag ggtgtcagcc aagaacgccc tggagtccta cgccttcaac    1860
atgaagagcg ccgtggagga tgaggggctc aagggcaaga tcagcgaggc ggacaagaag    1920
aaggttctgg acaagtgtca agaggtcatc tcgtggctgg acgccaacac cttggccgag    1980
aaggacgagt ttgagcacaa gaggaaggag ctggagcagg tgtgtaaccc catcatcagc    2040
ggactgtacc agggtgccgg tggtcccggg cctggcggct tcggggctca gggtcccaag    2100
ggagggtctg ggtcaggccc taccattgag gaggtggatt aggggccttt gttctttagt    2160
atgtttgtct ttgaggtgga ctgttgggac tcaaggactt tgctgctgtt ttcctatgtc    2220
atttctgctt cagctctttg ctgcttcact tctttgtaaa gttgtaacct gatggtaatt    2280
agctggcttc attatttttg tagtacaacc gatatgttca ttagaattct ttgcatttaa    2340
tgttgatact gtaagggtgt ttcgttccct ttaaatgaat caacactgcc accttctgta    2400
cgagtttgtt tgtttttttt tttttttttt tttttgcttt ggcgaaaaca ctacaaaggc    2460
tgggaatgta tgttttata atttgtttat ttaaatatga aaaataaaat gttaaacttt    2520
aaaaaaaaaa aaaaaaaaa aaaaaaaaa a                                    2551
```